(12) United States Patent  (10) Patent No.: US 8,477,307 B1
Yufa et al.  (45) Date of Patent: Jul. 2, 2013

(54) METHODS AND APPARATUS FOR BIOMEDICAL AGENT MULTI-DIMENSION MEASURING AND ANALYSIS

(76) Inventors: Ann Rachel Yufa, Colton, CA (US); Aleksandr Leybovich Yufa, Colton, CA (US)

( * ) Notice: Subject to any disclaimer, the term of this patent is extended or adjusted under 35 U.S.C. 154(b) by 1 day.

(21) Appl. No.: 13/374,976

(22) Filed: Jan. 26, 2012

(51) Int. Cl.
  *G01N 21/00* (2006.01)
(52) U.S. Cl.
  USPC .......................................... 356/338; 356/337
(58) Field of Classification Search
  USPC ................ 356/335–343, 27–28.5, 3.01–5.15, 356/432–444; 340/870.01–870.17
  See application file for complete search history.

(56) References Cited

U.S. PATENT DOCUMENTS

| | | | |
|---|---|---|---|
| 4,140,395 A | 2/1979 | Kreikebaum | |
| 4,189,236 A | 2/1980 | Hogg et al. | |
| 4,523,841 A | 6/1985 | Brunsting et al. | |
| 4,606,636 A | 8/1986 | Monin et al. | |
| 4,798,465 A | 1/1989 | Knollenberg | |
| 5,085,500 A | 2/1992 | Blesener | |
| 5,467,189 A | 11/1995 | Kreikebaum et al. | |
| 5,471,299 A | 11/1995 | Kaye et al. | |
| 5,495,105 A | 2/1996 | Nishimura et al. | |
| 5,515,164 A | 5/1996 | Kreikebaum et al. | |
| 5,731,875 A | 3/1998 | Chandler et al. | |
| 5,767,967 A | 6/1998 | Yufa | |
| 5,946,091 A | 8/1999 | Yufa | |
| 6,034,769 A | 3/2000 | Yufa | |
| 6,118,531 A * | 9/2000 | Hertel et al. | 356/336 |
| 6,346,983 B1 | 2/2002 | Yufa | |
| 7,087,444 B2 | 8/2006 | Wong et al. | |
| 7,283,215 B2 | 10/2007 | Wang et al. | |
| 7,439,855 B1 | 10/2008 | Yufa | |
| 7,573,573 B1 | 8/2009 | Yufa | |
| 8,017,408 B2 * | 9/2011 | Meinhart et al. | 436/168 |
| 8,050,729 B2 | 11/2011 | Shekalim | |
| 2007/0048746 A1 | 3/2007 | Su et al. | |
| 2008/0270042 A1 | 10/2008 | Wu et al. | |

* cited by examiner

*Primary Examiner* — Tri T Ton

(57) ABSTRACT

This invention, methods and apparatus for biomedical agent multi-dimension measuring and analysis, provide the multi-dimension measuring of the biomedical agents, cells, molecules, any and all explosive and hazardous agents, aerosol, airborne particles, liquid/fluid contaminations/particles, gas particles, etc. in order to recognize the multi-dimension size of the particles, select and sort them by their multi-dimension measurements, and count the particles in each sorted group. An improved apparatus for biomedical agent multi-dimension measuring and analysis comprises at least two light (laser) beam sources and at least two light detection means respectively located in the chamber. Also, the improved apparatus includes the amplifying, processing and control means providing distinguish and imaging of the particles/biomedical agents by their multi-dimensions, thereby, providing more precise agent grouping for analysis and counting.

6 Claims, 17 Drawing Sheets

View
41-41

View
42-42

View
43-43

METHODS AND APPARATUS FOR BIOMEDICAL AGENT MULTI-DIMENSION MEASURING AND ANALYSIS

FIELD OF THE INVENTION

The invention relates to the methods and apparatus for the detection, measuring, and analyzing (e.g., agent quantity and/or concentration counting, spectroscopic, radioactive, chemical, magnetic or infrared radiation analysis, etc.) of the agents including but not limited to the biological and biomedical agents, cells, molecules, any and all explosive and hazardous agents, aerosol, airborne particles, liquid/fluid contaminations/particles, gas particles, etc. More specifically, invention related to the multi-dimensional measuring and analysis of the biomedical agents.

BACKGROUND OF THE INVENTION

There are known many methods and devices for detecting and measuring of the biomedical agents (hereinbelow, the terms "biomedical agent" and/or "agent" and/or "particle" etc. solely and/or jointly accumulate the meanings of the biological, biomedical and biochemical agents, cells, molecules, any and all explosive and hazardous agents, aerosol, airborne particles, micro- and nano-particles, liquid/fluid contaminations/particles, gas particles, analytes, etc. Therefore, the use at least one of the terms does not exclude the other meanings for the used term, if otherwise not specified). The same if relevant for the terms, for example, such as "light" and/or "laser" and/or "electromagnetic energy", etc. [for instance, related to: "source(s)" and/or "beam(s), and/or "radiation(s)", etc.]. Further, only for simplification of the disclosure the term "biomedical agent" can mostly be presented by the term "agent" or "particle", and the term "laser" by the term "light").

Some of them are useful for detection and measurement of the agents illuminated by the light (laser) beam.

There are well known devices and methods of agent (particle) measurement utilizing an open cavity laser and a light scattering techniques. These methods and devices mostly use the optic systems, which are based on the lens use, the same as it described, for example, in U.S. Pat. Nos. 4,140,395; 4,798,465 and 5,495,105.

The other known devices (for example, U.S. Pat. No. 4,606,636) use the mirror systems, e.g., a divergent quadric reflector. Such mirror based devices use a hemi-paraboloidal sphere as a mirror.

In the U.S. Pat. Nos. 4,189,236; 4,523,841; 5,467,189 and 5,515,164) are described the devices (sensors) with non-divergent ellipsoidal mirrors, which also, for example, described in the U.S. Pat. Nos. 5,767,967; 5,946,091; 7,439,855 and 7,573,573, instead of the lens systems or divergent quadric mirrors.

All these devices, mentioned in the prior art above, use the light scattering focalizing methods. Such methods are based on the collection of the scattered light. A light scattering occurs at the first focal point (focus) 8 by particles in the laser beam (in the point of intersection of the particle and light (laser) beam). Considering stochastic dispersion of the scattered light, the devices, mentioned in the above prior art, use mirrors or optics. This is necessary for scattered light collecting and focalizing at the second focal point (focus) 9, where a light detector is placed and intended for scattered light detection [see FIGS. 1, 2, 3, 4 (prior art)].

The FIGS. 1 (prior art)-4 (prior art) (see also FIGS. 1-4 in the U.S. Pat. No. 6,034,769) depict the most common known principles of the light scattering by the open cavity laser: in FIG. 1 (prior art), related to the use of the optics (see the U.S. Pat. Nos. 4,140,395; 4,798,465 and 5,495,105), is shown that the scattered light is collected by the optical system, which is presented by the lenses 10 [also in FIGS. 1-4 (prior art): 1—a device axis, 2—a single light beam axis, 3—a particle flow axis, 5—a plurality of the light detection means (or a large size detection means), 6—the collected scattered light, 8—a first focal point, 9—a second focal points]; in FIG. 2 (prior art) is presented the device, using divergent quadric mirror (U.S. Pat. No. 4,606,636), and from FIG. 2 (prior art) is understandable that the collection of the scattered light is provided by the divergent quadric (paraboloidal) mirror 18; in FIG. 3 (prior art) the counting and measuring devices (sensors), mentioned in the U.S. Pat. Nos. 4,189,236; 4,523,841; 5,467,189 and 5,471,299, use the ellipsoidal mirrors 17; in FIG. 4 (prior art) is presented the particle sensor (measuring and counting device) by U.S. Pat. No. 5,515,164, also using the ellipsoidal mirror for the scattered light collection. This sensor uses specially increased cross-section outlet area of the particle flow. It is understood, that the methods and devices, of the prior art mentioned above, require the use of the scattered light collection means/systems [FIGS. 1-4 (prior arts)]. Such methods and/or devices need to include expensive means and systems. Also, the mentioned above prior art methods and devices have a common deficiency, which is characterized by non-consideration of all scattered light plurality [for example, the unconsidered scattered light 23 in FIGS. 1-4 (prior arts)] and non-precise focalizing of the particle flow [for example, the unfocused scattered light 7 in FIGS. 1-4 (prior arts)].

Some known devices (for example, by U.S. Pat. No. 5,731,875) use a plurality of light emitting low power lasers which provide the elimination of the laser heat-sink, but, it requires to use a plurality of fiber optic stands and the optical element(s) for the focusing of a plurality of light beams, but it will still be a plurality of the beams after collecting optics [not the one (single) enhanced (combined) powerful laser beam] considering that in this patent are used the lasers, which produce the monochromatic coherent light beams (laser beams), which are not combinable into one single powerful beam. Therefore, the particle will intersect not the one single powerful laser beam, but the plurality of the low power laser beams, thereby, creating the incorrect information regarding quantity of the agents (particles) in the assayed (analyzed) specimen.

Thus, the unfocused and/or unconsidered (undetected) scattered light in the mentioned above devices of a prior art creates a light background (light noises) inside such devices, thereby creating incorrectness of the resulting information about the measured agents. Also, such light noises limit the sensitivity of the mentioned devices.

Additionally to the devices using the scattered light collection, there are known the devices using some other optic detection methods, for example, by light splitting, etc.

There are also known some methods and devices useful for detection and measurements of the agents (e.g., airborne agents, etc.) using Raman scattering techniques.

It is well known, that the molecules can be airborne agents, including but not limited to explosives, narcotics, hazardous chemicals, or other chemical or non-chemical species, etc.

As it is well known, the Raman spectroscopy is a technique desired for molecular detection and molecular dynamics studies. Surface Enhanced Raman Scattering (SERS) improves the sensitivity by amplifying the original Raman scattering intensity. The complex plasmon resonance of single nanoparticles and the plasmon correlation with the adjacent nanoparticles are the focus of the biomedical field.

The most SERS grounds of nanoparticle combinations related and depend on the size of the particles. It is known, that the SERS spectroscopy is useful to provide a chemical-bond information and biomolecular flat imaging.

The characteristics of the nanoparticles are extremely useful for in vitro and/or in vivo diagnostic analysis and/or imaging. One such characteristic of nanoparticles is the size of the particles.

For example the U.S. Pat. Nos. 7,283,215 and 7,087,444, and the U.S. Patent Publications Nos. 2007/0048746 and 2008/0270042 describe the devices of detection of the airborne agents in microfluidics. It is known, that microfluidics is a field of work that deals with the fluid-based transport of mass, and that the microfluidic channels are generally enclosed and not in direct relation with the surrounding environment (e.g., atmosphere, etc.).

Another U.S. Pat. No. 8,017,408 also describes the method and device of detection of the airborne agents using SERS principles for particle detection and microfluidics, utilizing free-surface fluidics. In general, the disclosure provides a microfluidic platform for real time sensing of volatile airborne agents, such as explosives. The device provides the multiple length scales, ranging from tens of micrometers to a few nanometers. Free-Surface Fluidics (FSF), are used such that one or more fluid surfaces of a fluid flow channel flow are exposed to the surrounding atmosphere, with confinement being caused by surface tension forces operating, typically, on open-channel flows of order depth. This free-surface fluidic (FSF) architecture is incorporated with Surface Enhanced Raman Spectroscopy (SERS) for detection of airborne agents.

The FSF architecture provides at least on of a plurality of surfaces of the microfluidic flow to be exposed to the atmosphere. Since the length scale is on the order of a few microns, a very large surface area is exposed to the atmosphere. This provides automatic injection of airborne molecules into the microfluidic channel.

The disclosure provides a free-surface detection device comprising: a substrate; a fluid flow channel having a first end and a second end located in or on the substrate; at least one free-surface interface region located between the first end and the second end, wherein the free-surface interface region is open on at least one side to atmospheric air comprising an analyte; an excitation area, wherein electromagnetic energy excites a SERS probe in a fluid flowing in the fluid flow channel containing analytes; and a detection area, wherein a scattered light is detected by a detection device, wherein the free-surface interface region is in fluid communication with the excitation and detection areas.

Such methods and devices use the direct detection principles avoiding the delivering and/or collecting optics or mirrors. Also such methods and devices provide the Raman spectroscopy, but do not analyze the quantity and/or concentration of the agents (particles) which are presented at least by two dimensions or preferably by three dimensions.

The disclosure also describes a method for analyte detection comprising: providing a flow of a fluid through a fluid channel in a fluidic device, the fluidic device comprising: a substrate; a fluid flow channel having a first end and a second end located in or on the substrate; at least one free-surface interface region located between the first end and the second end, wherein the free-surface interface region is open on at least one side to atmospheric air comprising an analyte; an excitation area, wherein electromagnetic energy excites a SERS probe in a fluid flowing in the fluid flow channel containing analytes; and a detection area, wherein the scattered light is detected by a detection device, wherein the free-surface interface region is in fluid communication with the excitation and detection areas and wherein analytes in the sample are absorbed into the fluid; a laser source that emits light at the excitation area; and a detector that detects the scattered light from excited SERS probes, contacting the fluid with a SERS probe; and measuring emissions of SERS probes aggregated within the fluid with an analyte, wherein the scattered light is indicative of the presence of analyte in the sample.

More specifically the device comprises a substrate upon which or within which a reservoir or inlet is fluidly connected to an outlet by a fluid channel. The reservoir or inlet is about 40 µm deep (where "µm" means micron). Fluid channel comprises contiguous different regions having a proximal fluid flow region, free-surface interface region and distal fluid flow region. Also the device includes the first region and the detection region, which, when present, are approximate locations in the distal fluid flow region, or in the free-surface interface region. The first regions and detection coincide. During the use of the Raman principles, fluorescent or infrared radiation spectroscopy, regions coincide based upon excitation and emission timing. This prior art invention provides fluidic devices that can drive and guide liquid flow in microfluidic channels to transport biomolecules and living cells.

Such devices, providing the particle direct detection, do not differentiate (distinguish) and/or recognize the particles by their spatial form (shape), and do not provide the counting of particles (e.g., microparticles or nanoparticles, etc.) and/or specific analytes (for instance, in biomolecules and living cells, etc.) in vitro and/or vivo diagnostic testing with respect to the particle spatial size.

There is known the other inventions intended for analysis of a constituent of body fluid using the fluidic channel (e.g., U.S. Pat. No. 8,050,729).

Another known method, also using the scattered light direct detection principles, is described in U.S. Pat. No. 5,085,500. The scattered light in this device is detected by a plurality of light detectors 5 directly with no scattered light optic and/or mirrors collection. In FIG. 5 (prior art) [see also FIG. 5 (prior art) in the U.S. Pat. No. 6,034,769 and FIG. 4a in U.S. Pat. No. 5,085,500] is shown a simplified drawing of the device (U.S. Pat. No. 5,085,500), using the scattered light direct detection method.

It is understood, that the mentioned method and device, require the use of the very large spatial surface (e.g., cylindrical, etc.) of the light detector or sufficient quantity of the light detectors surrounding the focal point. Such method and/or device need to include expensive detection means and systems. Also, the mentioned above method and device have an additional common deficiency, which is characterized by non-consideration of all scattered light [for example, a scattered light 23 in FIG. 5 (prior art)].

The U.S. Pat. No. 6,034,769 describes the method and device for particle direct detection, which is free of the deficiencies of the U.S. Pat. No. 5,085,500 using the scattered light collection principles. The methods and device by U.S. Pat. No. 6,034,769 provide the precise measuring and counting of the micro- and nano-particles.

According to the U.S. Pat. No. 6,034,769, a single light or laser beam of the single light source intersects a particle flow (along axis 3 of the particle flow means 26) within the particle monitoring region in the area of the single light detection means which is placed on a single light beam axis 2. The active area (e.g., photoelement, etc. [not shown]) of the single light detection means 4 (e.g., photodetector/pho-todiode, etc.) of this prior art is fully exposed to the single light beam, as it is shown in FIG. 6 (prior art) [see also FIGS. 6, 7 of the U.S. Pat. No. 6,034,769].

The mentioned hereinabove methods and devices provide one dimension (size) measuring (not spatial, e.g., such as an imaging) of the agents/particles, therefore, such methods and devices can not differentiate/distinguish and/or recognize the form/shape of the analyzed biomedical agents and more particularly can not differentiate/distinguish and/or recognize the form/shape of the analyzed microorganism, cell, molecule and/or analyte in vitro and/or in vivo diagnostic analysis and/or imaging, etc.

Therefore, the mentioned known methods and devices have the described above deficiencies which are eliminated in the improved methods and apparatus for biomedical agent multi-dimension measuring and analysis.

Considering that some microorganisms or cells can have a specific spatial form/shape, for example, an elongated (e.g., "worm"-alike) form or regular or irregular spherical-alike form, etc., the more convenient to recognize and identify (verify) the biological organisms by their forms, for example, before the complex analysis of their spectroscopic, chemical, magnetic, etc. characteristics. Also, it is more precise and authentic to recognize, select and sort the particles by their, for example, three-dimensions (X, Y, Z), but not only by the particle's single size (e.g., X-axis measurement). Additionally, the improved method and apparatus provide possibility to spatially depict/display the multi-dimension measured particles.

While the mentioned above prior art fulfill their respective, particular objectives and requirements, the mentioned prior art inventions do not disclose, teach and/or suggest the methods and apparatus for biomedical agent multi-dimension measuring and analysis including the steps (and their sequence) of the methods and elements (components/parts) of the apparatus providing the possibility of the differentiation/distinguishing and/or recognition of the form/shape of the analyzing microorganism, cell, molecule and/or analyte in vitro and/or in vivo diagnostic analysis and/or imaging, etc.

Those skilled in the art will readily observe that numerous modifications and advantages of the improved methods and apparatus for biomedical agent multi-dimension measuring and analysis may be made while retaining the teachings of the invention.

Thus, the known prior art do not provide the efficient, precise, and convenient methods and apparatus for biomedical agent multi-dimension measuring and analysis according to the present invention substantially departs from the devices of the prior art.

OBJECT AND ADVANTAGES OF THE INVENTION

Accordingly, several objects and advantages of the present invention are to provide the improved methods and apparatus for biomedical agent multi-dimension measuring and analysis:

It is object of the invention to provide the improved methods and apparatus which provide the multi-dimension measurement of the agents/particles.

It is another object of the invention to provide an improved methods and apparatus with the increased precision of the particle measuring.

It is further another object of the invention to provide an improved methods and apparatus with the increased authenticity of the particle size.

It is still further an object of the invention to provide an improved methods and apparatus with the increased authenticity of the information about agents, airborne, gas, liquid particles and/or biomedical microfluidic micro- and nano-particles.

It is further object of the invention to differentiate/distinguish the agents/particles by their form (shape).

It is still an object of the invention to provide a convenience to recognize and identify (verify) the biomedical (biological) organisms by their forms, before to analyze, for example, their biological, chemical, magnetic, etc. characteristics.

It is still an object of the invention to provide a selection and sorting particles by their multi-dimensions (three dimensions: X, Y, Z), but not only by their single size (e.g., X-axis measurement).

It is still an object of the invention to provide multi-dimension image of the spatially measured particles.

It is also another object of the invention to provide the counting of the multi-dimension measured particles and/or their concentration.

It is still another object of the invention to provide an improved methods and apparatus with the increased efficiency of the measuring and counting processes and processes of analyzing of the particle concentration.

It is yet another object of the invention to reduce the light noises by specific shielding each of a plurality of the light detection means used for the multi-dimension particle measuring.

It is another further object of the invention to provide an improved the increased sensitivity of the particle size detection by specific shielding each of a plurality of light detection means.

Still, further objects and advantages will become apparent from a consideration of the ensuing description accompanying drawings.

DESCRIPTION OF THE DRAWING

In order that the invention and the manner in which it is to be performed can be more clearly understood, embodiments thereof will be described by way of example with reference to the attached drawings, of which.

It is understood, that these illustrations and drawings are the examples of the improved apparatus configurations and architectures, and those skilled in the art will readily observe that numerous structures, modifications and advantages of the improved methods and apparatus for biomedical agent multi-dimension measuring and analysis may be made while retaining the teachings of the present invention.

SUMMARY OF THE INVENTION

In view of the foregoing disadvantages inherent in the known prior art, the present invention provides an improved methods and apparatus for biomedical agent multi-dimension measuring and analysis. As such, the general purpose of the present invention, which will be described hereinafter in greater details, is to provide the improved methods and apparatus with the multi-dimension measuring and analyzing of the biomedical agent. The improved methods and apparatus have many of the advantages of the biomedical agent multi-dimension measuring and analysis mentioned heretofore and many novel features that result in the efficient and precise biomedical agent multi-dimension measuring and analysis, which is not anticipated, rendered obvious, suggested or even implied by any of prior art methods and devices for agent/particle measuring, either alone or in any combination thereof.

This invention, methods and apparatus for biomedical agent multi-dimension measuring and analysis, provides the multi-dimension measuring of the biomedical agents, cells, molecules, any and all explosive and hazardous agents, aerosol, airborne particles, liquid/fluid contaminations/particles, gas particles, etc. in order to recognize the multi-dimension size of the particles, select and sort them by their multi-dimension measurements, and count the particles in each sorted group.

To attain this, the present invention generally comprises at least two light (laser) beam sources and at least two light detection means respectively located in the chamber. Also, the improved apparatus includes the amplifying, processing and control means providing distinguishing and imaging of the particles/biomedical agents by their multi-dimensions, thereby, providing more precise agent grouping for further counting and analysis.

DESCRIPTION OF THE PREFERRED EMBODIMENTS

With reference now to the drawings, and particularly to FIGS. 1-16 thereof, an improved methods and apparatus for biomedical agent multi-dimension measuring and analysis embodying the principles and concepts of the present invention.

As it has been mentioned hereinabove, the terms "particle" and/or "agent", etc. hereinbellow solely and/or jointly accumulate the meanings of the biological agents, cells, molecules, any and all explosive and hazardous agents, aerosol, airborne particles, liquid/fluid contaminations/particles, gas particles, analytes, etc. Therefore, the use at least one of the terms does not exclude the other meanings for the used term, if otherwise not specified.

Figure 1:
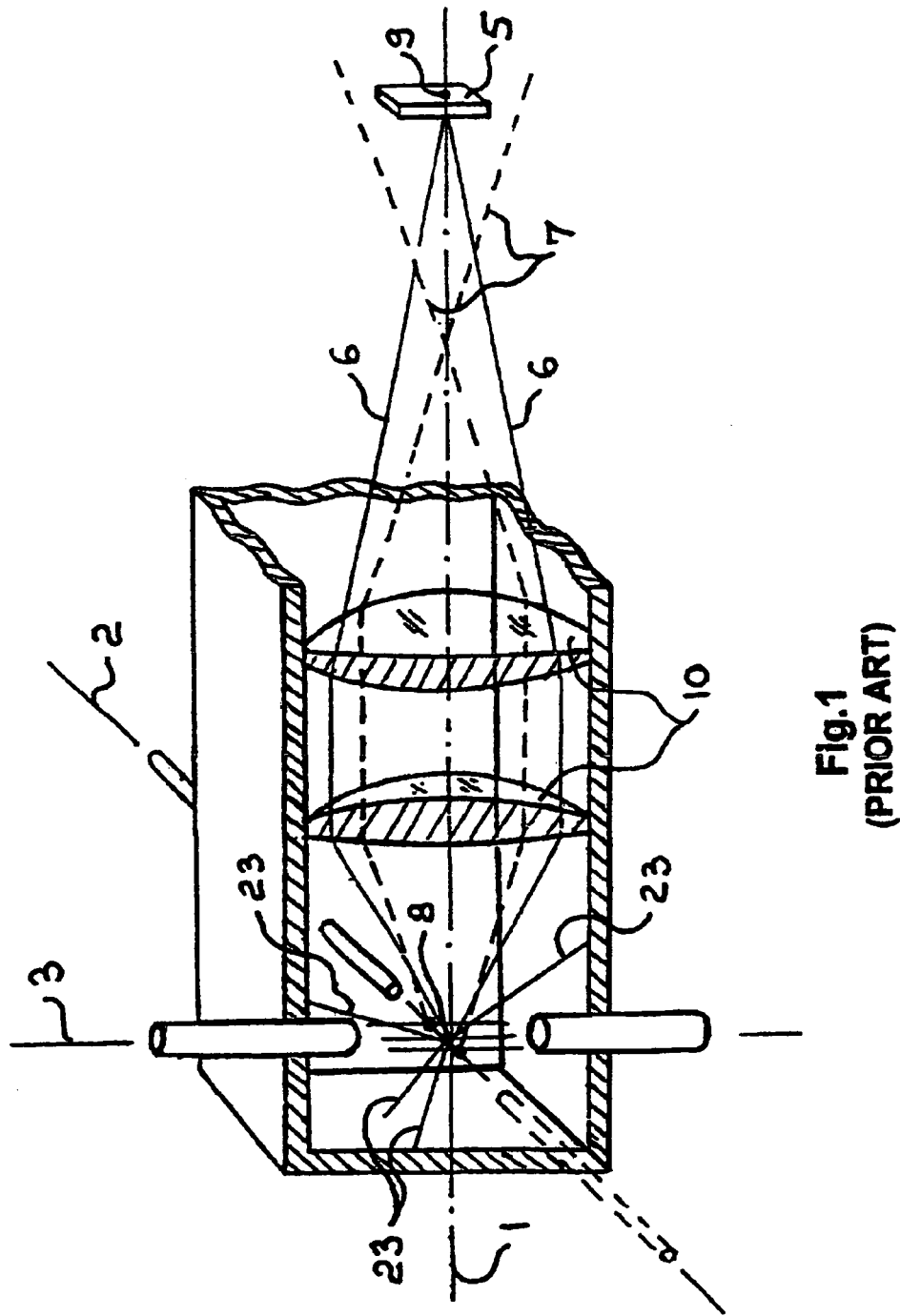
FIG. 1 (prior art) is a presentation of the scattered light collection by an optics in the prior art.
Figure 2:
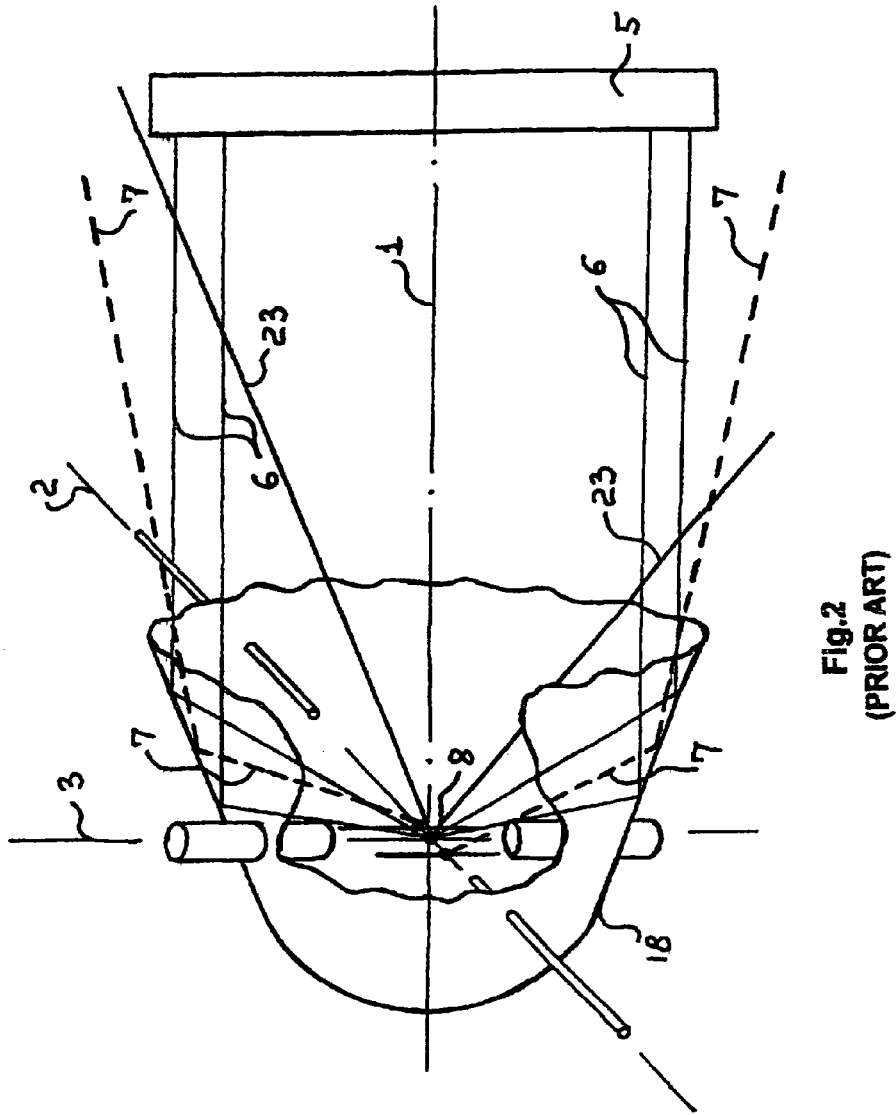
FIG. 2 (prior art) is a presentation of the scattered light collection by a non-divergent quadric mirror in the prior art.
Figure 3:
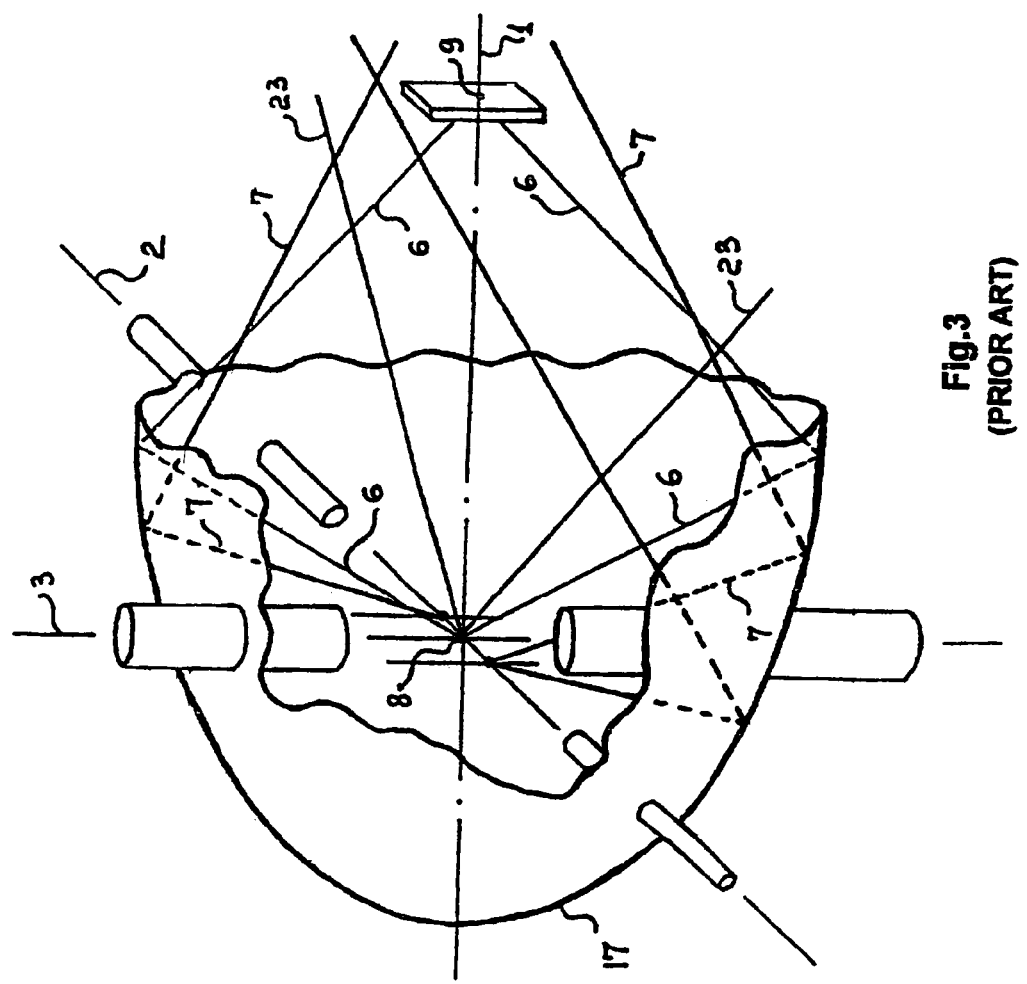
FIG. 3 (prior art) is a presentation of the scattered light collection by an ellipsoidal mirror in the prior art.
Figure 4:
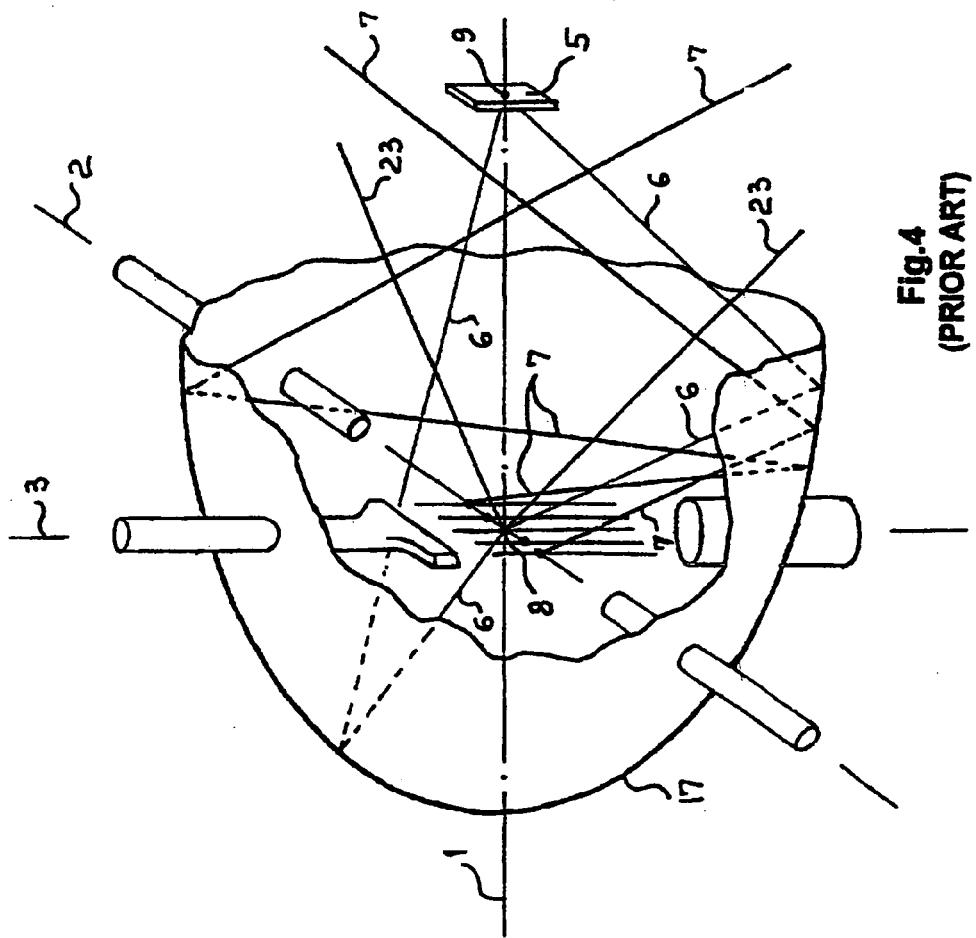
FIG. 4 (prior art) is a presentation of the scattered light collection by an ellipsoidal mirror with the especially increased inlet cross-sectional area of the particle flow in the prior art.
Figure 5:
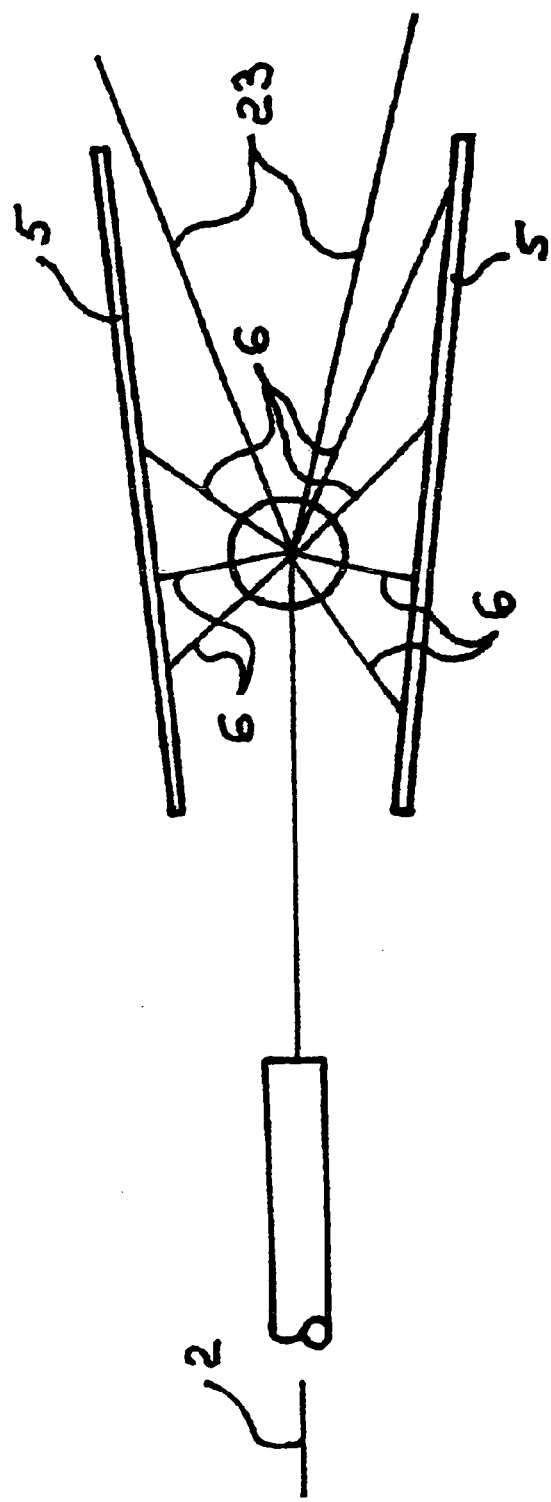
FIG. 5 (prior art) is a presentation of the scattered light direct detection method in the prior art.
Figure 6:
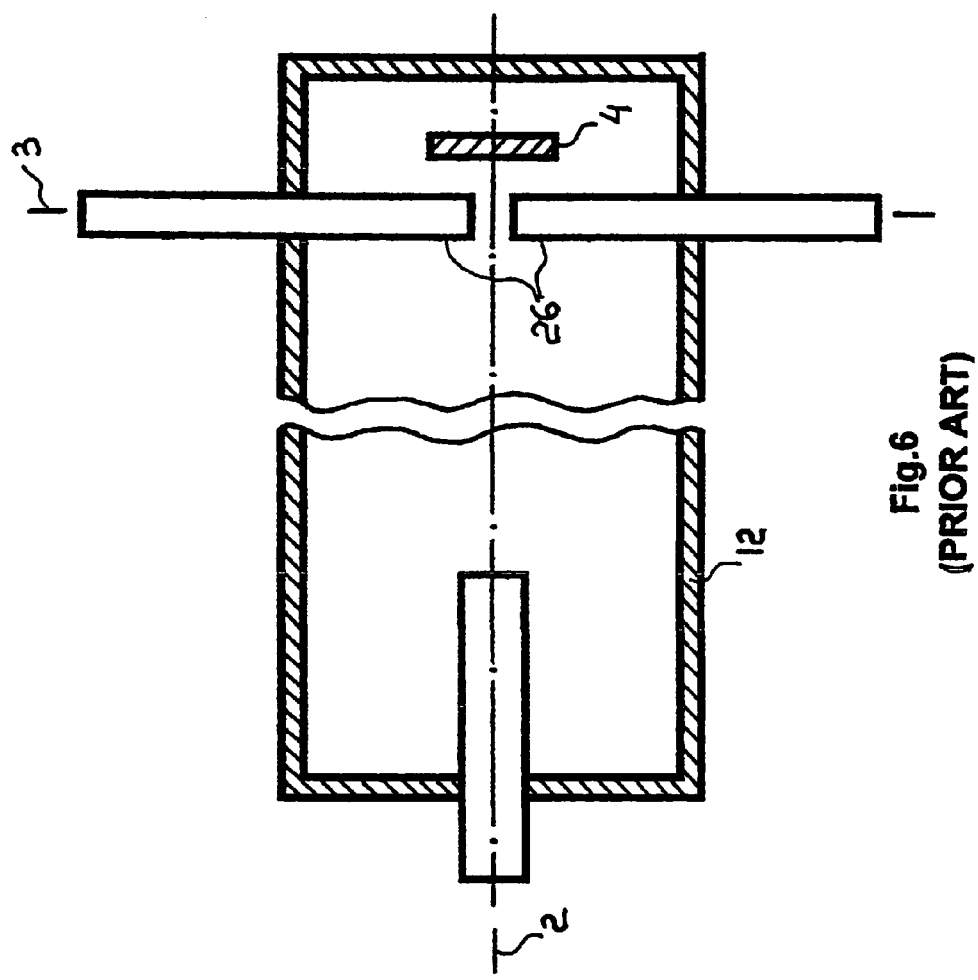
FIG. 6 (prior art) is a presentation of the light direct detection method in the prior art.
Figure 7:
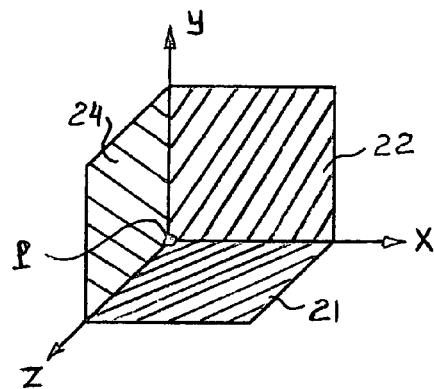
FIG. 7 is a simplified spatial illustration of the examples of the directions for the agent multi-measurements in the improved apparatus for biomedical agent multi-dimension measuring and analysis.

In the FIG. 7 are shown the spatial coordinate system XYZ including three planes: plane XPZ 21, plane XPY 22 and plane YPZ 24. The axes X, Y and Z intersect each other at the point "P" [X=0, Y=0, Z=0] (see also FIG. 8).

The multi-dimension measuring can be provided by at least two-dimension measurements in the direction along the axes X and Y (XPY plane 22) or axes X and Z (XPZ plane 21) or axes Y and Z (YPZ plane 24) in order to provide at least two-dimensions of a plane (flat) image of the agent/particle/analyte in the assayed specimen, and further provide recognition of the particles by two-dimensions, but not by one dimension.

Figure 8:
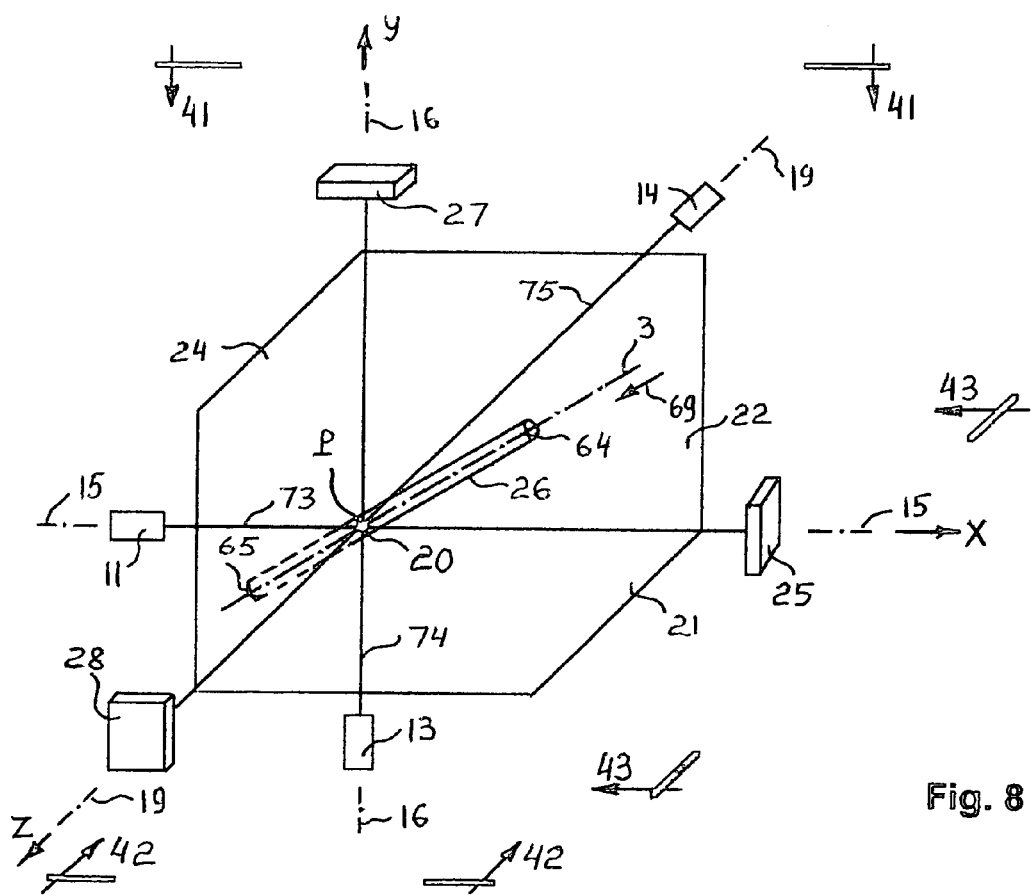
FIG. 8 is a simplified illustration of the light beam emissions, particle flow channel, and particle detection elements disposition in the improved apparatus.

In the FIG. 8 are conditionally shown the three-dimensions measurement (the three dimension measurement is also known as a "3-D" measurement) of the particles spatially, including the micro- and/or nano-particles and/or microorganisms, cells, molecular and/or analytes in the microfluidic biomedical substance. According to FIG. 8, the improved apparatus comprises a first light (laser) beam source 11, a second light (laser) beam source 13 and a third light (laser) beam source 14. In the FIG. 8 is conditionally shown that the first light beam axis 15 of the first light beam 73 from the first light beam source 11 coincides with the axis X of the coordinate system XYZ, the second light beam axis 16 of the second light beam 74 from the second light beam source 13 coincides with the axis Y of the coordinate system XYZ, and the third light beam axis 19 of the third light beam 75 from the third light beam source 14 coincides with the axis Z of the coordinate system XYZ. It is understood, that the first light beam 73 from the first light (laser) beam source 11 is radiated along the first light beam axis 15, the second light beam 74 from the second light (laser) beam source 13 is radiated along the second light beam axis 16, and the third light beam 75 from the third light (laser) beam source 14 is radiated along the third light beam axis 19. As shown in FIG. 8, the first light detection means 25 (LDM 1) is located along YPZ plane 24, the second light detection means 27 (LDM 2) is located along XPY plane 22, and the third light detection means 28 (LDM 3) is located along XPZ plane 21 (see also the FIG. 10a). The particle/agent flow is provided (e.g., by pumping means or blowing means, etc. [not shown]) along particle/agent flow axis 3 through the particle flow tubular means 26. As an example, the location of the particle flow tubular means 26 with respect to the axes X, Y, Z and to the coordinate planes is shown in the FIGS. 9a-9c.

Figure 9A:
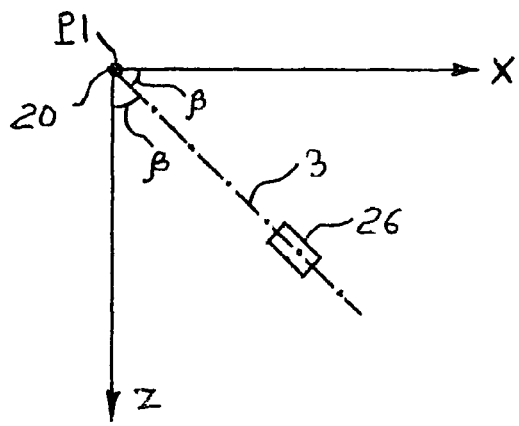
FIG. 9*a* is a simplified projection (view 41-41) of the particle flow tubular means on the plane XPZ.
Figure 9B:
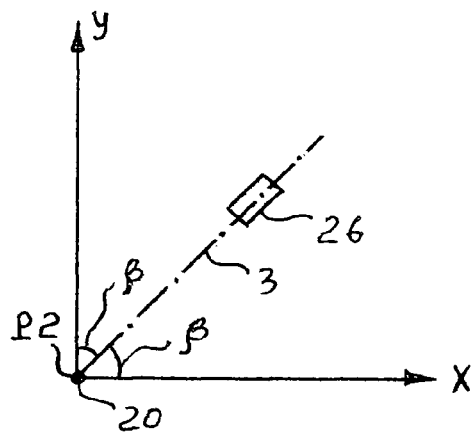
FIG. 9*b* is a simplified projection (view 42-42) of the particle flow tubular means on the plane XPY.
Figure 9C:
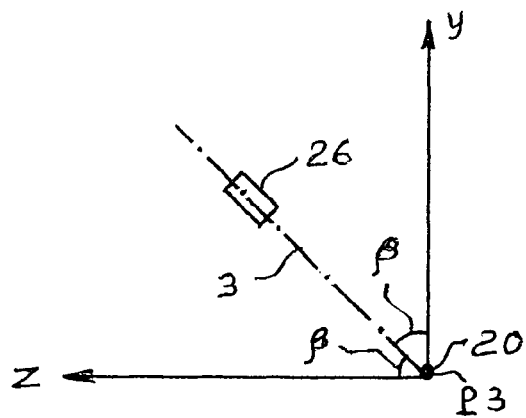
FIG. 9c is a simplified projection (view 43-43) of the particle flow tubular means on the plane YPZ.

The FIGS. 9a, 9b, 9c illustrate the projections (views 41-41, 42-42, 43-43) of the particle/agent flow axis 3 on the planes XPZ 21, XPY 22 and YPZ 24 (wherein: P1—a point of intersection of the axes X and Z [X=0, Z=0], P2—a point of intersection of the axes X and Y [X=0, Y=0], P3—a point of intersection of the axes Y and Z [Y=0, Z=0]). It is conditionally shown in FIGS. 9a-9c, that the angle β=45°, but the angle β can be of any reasonable value except of 0°, 90°, –90°, 180°, –180°, 270°, –270°, 360° and preferably except the values of the angles closed to these angles in order to avoid the coincidence or approximate coincidence of the particle flow axis 3 with the any axis of the axes X, Y, Z (FIG. 8) and the light beam axes 15, 16, 19 (FIGS. 13a-15). It is understood, that there can be any other reasonable location of the particle flow tubular means 26, and under any other reasonable and convenient angles to the coordinate planes.

Figure 10A:
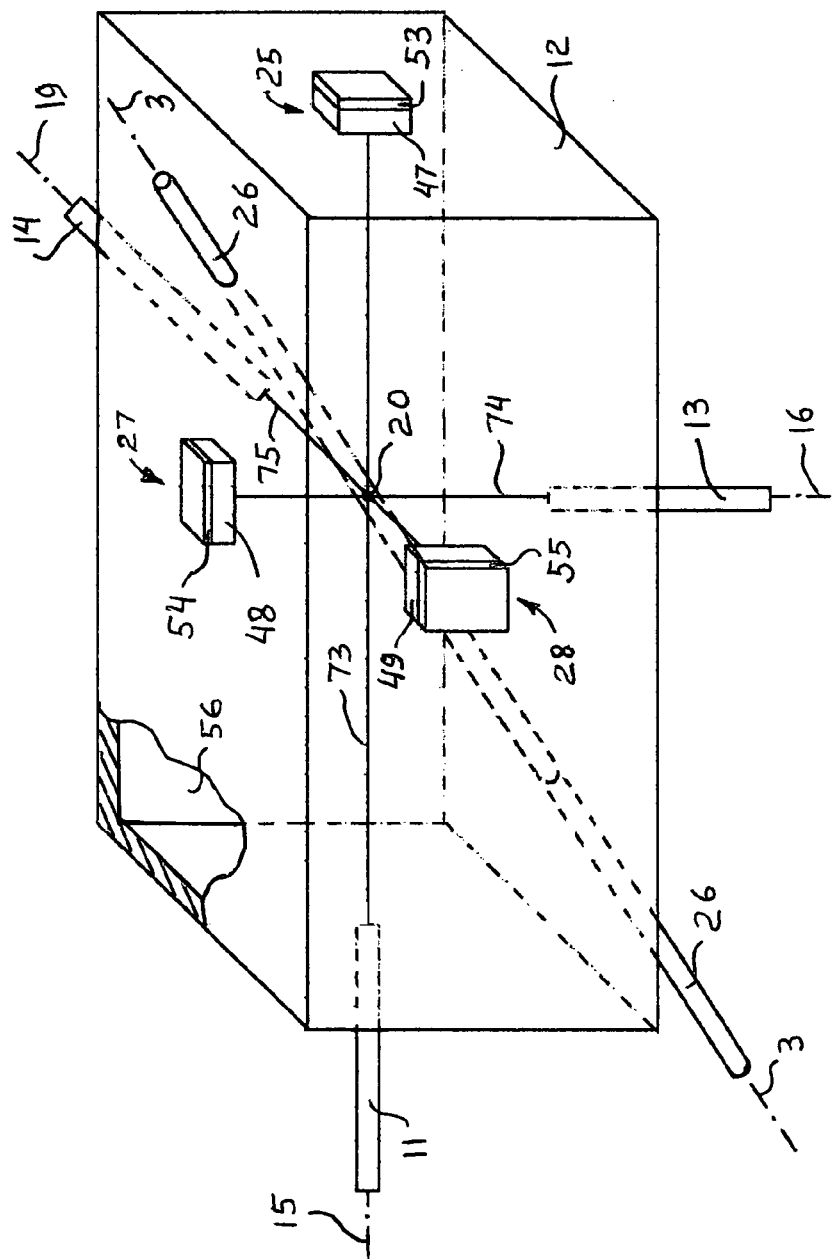
FIG. 10a is a simplified drawing of the chamber assembly.

In FIG. 10a is conditionally shown the chamber 12 of the rectangular configuration, but the chamber 12 can be of any reasonable geometric regular or irregular configuration and/or form/shape (e.g., square [cubic], cylindrical form, etc.) and size. The inside of the chamber 12 can be coated (painted, etc.) by the black flat (mate, rough) coating 56, absorbing possible reflected (scattered) light, thereby eliminating (or at least reducing) possible light background (light noises).

Figure 11:
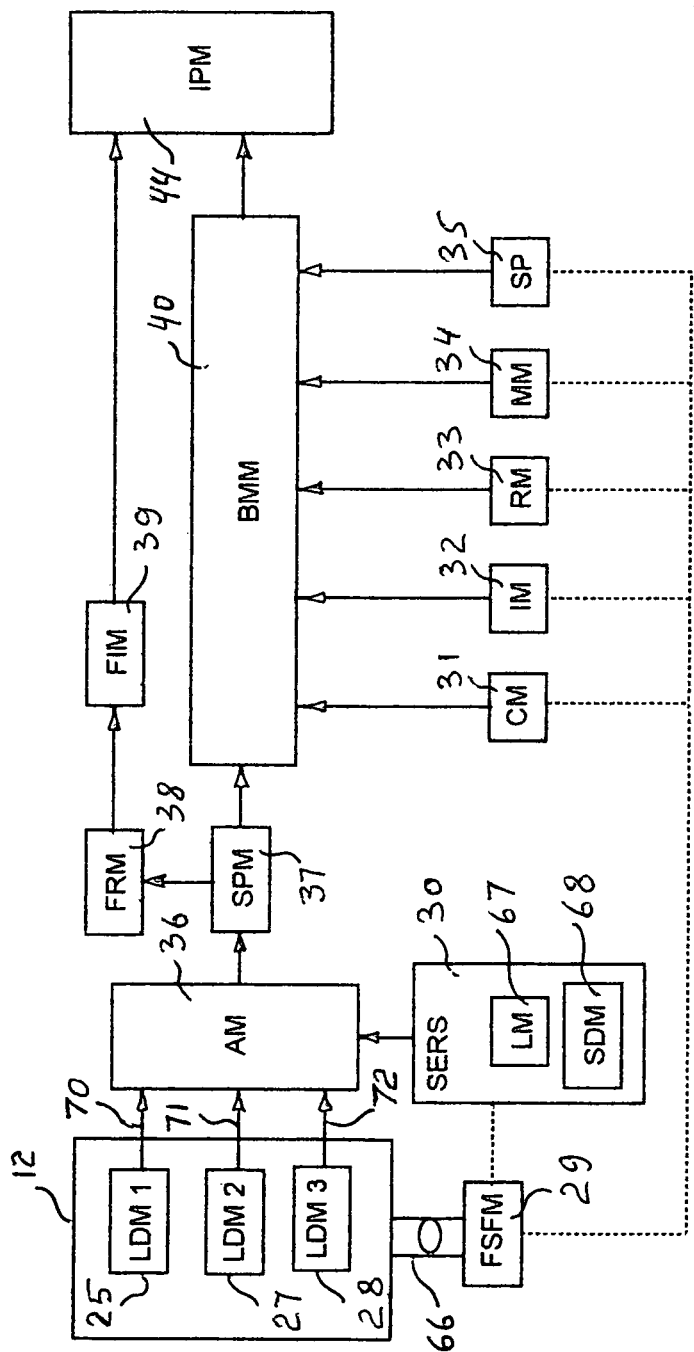
FIG. 11 is a simplified general schematic of the improved apparatus.
Figure 12:
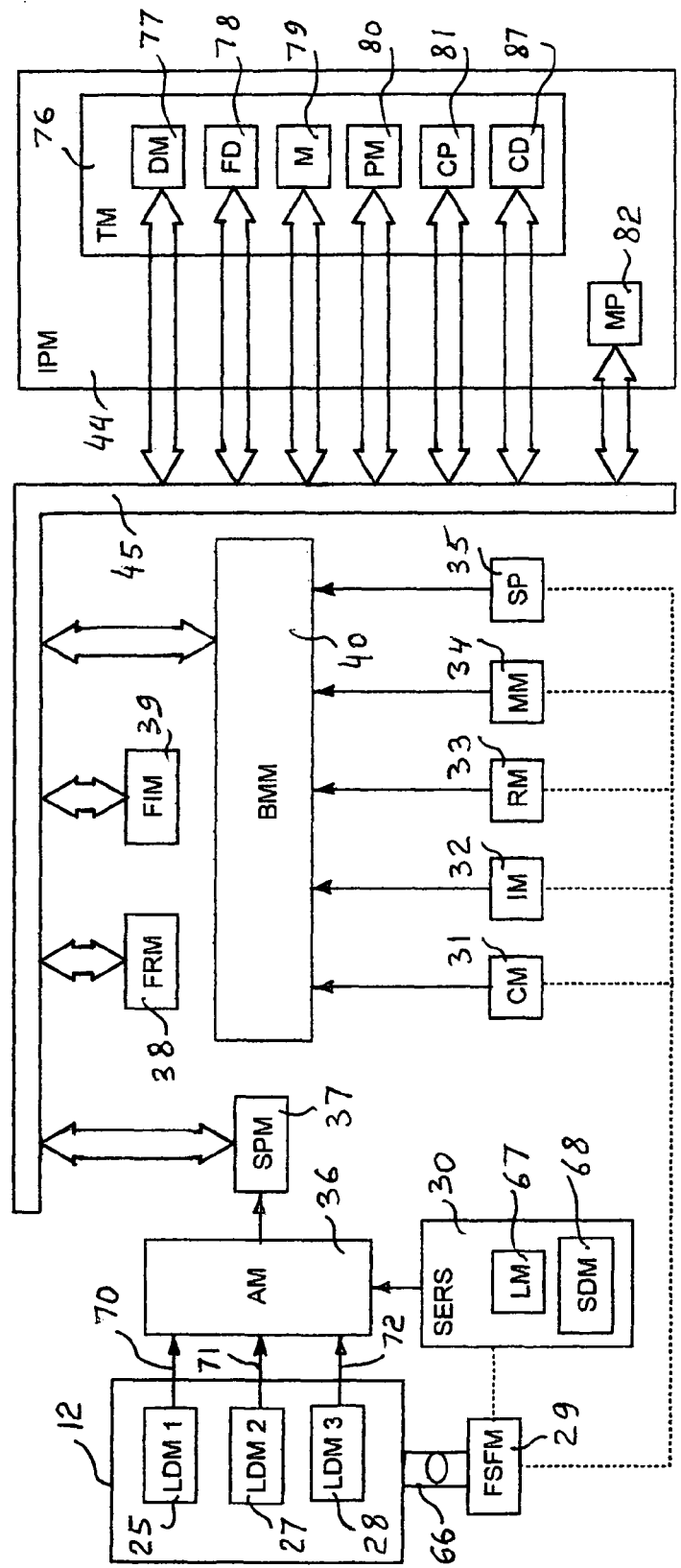
FIG. 12 is a simplified schematic of the improved apparatus with the multiplexed bus.

The inlet end (not shown) of the free-surface microfluidic means 29 (FSFM) for the biomedical particle (analyte) analysis can be extended (not shown) from the outlet end 65 of the particle flow tubular means 26 (see FIGS. 8, 13a,b) or can be coupled (FIGS. 11, 12) with the particle flow tubular means 26 (e.g., with the outlet end 65 [not shown in FIGS. 11, 12] of the particle flow tubular means 26). The free-surface microfluidic means 29 can be coupled with the other biomedical equipment (FIGS. 11, 12) providing radioactive and/or X-Ray absorption techniques (RM) 33, infrared (IM) 32, visible (not shown), ultraviolet (not shown), magnetic (MM) 34 and/or electromagnetic techniques, electromagnetic radiation absorption techniques (not shown), mass spectroscopy techniques (SP) 35, liquid chromatography techniques (not shown), flame ionization analysis techniques (not shown), DNA melting point techniques (not shown), or titration analysis techniques (not shown), chemical analysis techniques (CM) 31, etc. (see FIGS. 11, 12).

Figure 13A:
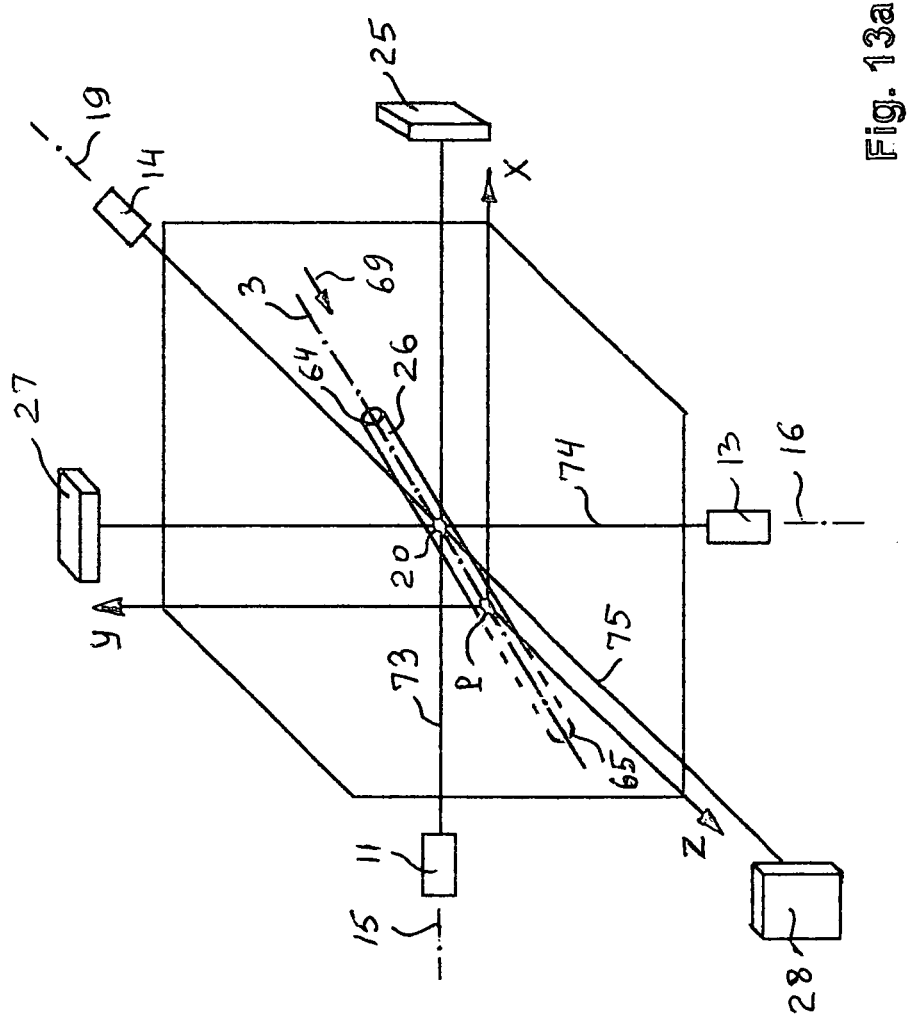
FIG. 13a is a simplified first illustration of the light beam emissions, light detection means and uninterrupted particle flow tubular means disposition and their axes intersection.
Figure 14:
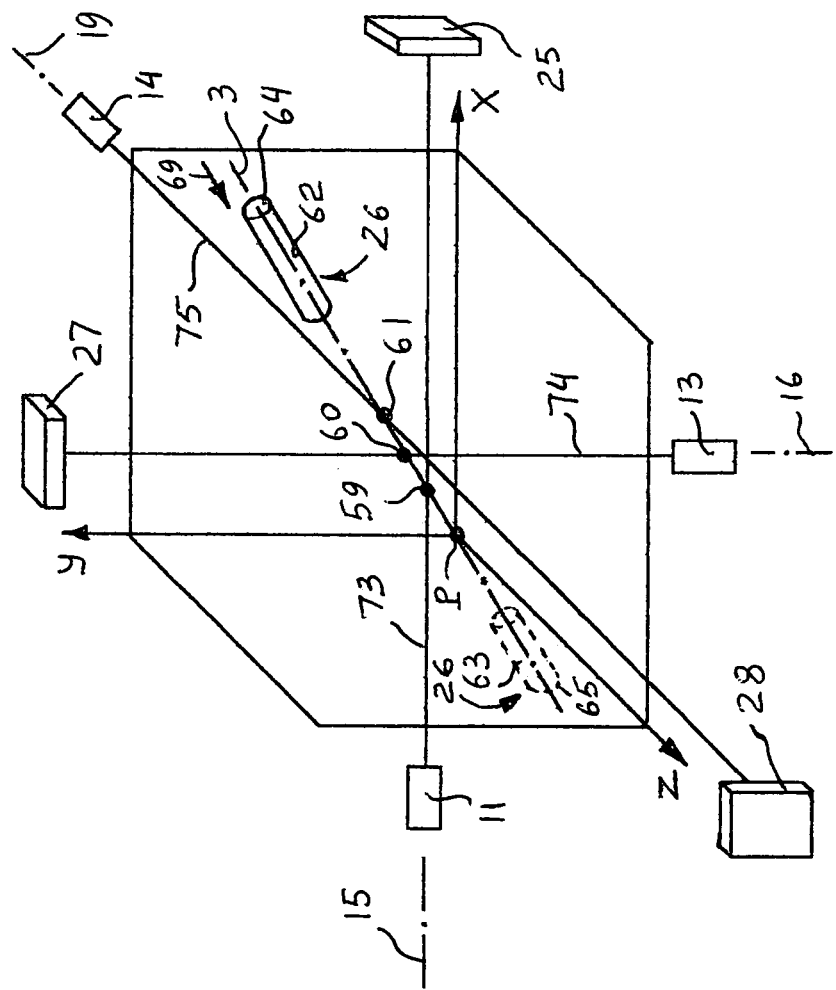
FIG. 14 is a simplified illustration of the light beam emissions, light detection means and interrupted particle flow means disposition.

The particle flow tubular means can be of an uninterrupted (undivided) configuration as it is shown, as an example, in FIGS. 8, 10a, 13a,b (e.g., the particle flow tubular means can be of an uninterrupted configuration for microfluidic biomedical substance, liquid, water, aerosol assayed specimen, etc.) or can be of interrupted (divided) configuration comprising the inlet portion 62 and outlet portion 63, as it is shown in FIG. 14, (e.g., the particle flow tubular means can be of an interrupted configuration for airborne, gas specimen, etc.). The inlet end (not shown) of the free-surface microfluidic means 29 for SERS of the biomedical particle (analyte) analysis can be extended (not shown) from the outlet end 65 of the interrupted particle flow tubular means 26 (see FIG. 14) or can be coupled (FIGS. 11, 12) with the outlet end 65 of the interrupted particle flow tubular means 26. The free-surface microfluidic means 29 can be coupled with the other biomedical equipment (FIGS. 11, 12) mentioned hereinabove and partially shown in FIGS. 11, 12.

The particle flow tubular means 26 is a part of the particle flow channel (not shown), and the inlet end 64 (FIGS. 8, 13a-15) of the uninterrupted or interrupted particle flow tubular means 26 can be extended from or coupled with the particle flow channel (not shown) which is coupled with the specimen assaying pumping means (not shown) or blowing means (not shown) providing the particle flow, for example, in the direction 69 (FIGS. 8, 13a-16).

The particle flow tubular means 26 can be of any reasonable geometric configuration, for example, can be of cylindrical or square cross-sectional form, etc. and made of the material, which is transparent for the light (laser) beam (e.g., for the uninterrupted particle flow tubular means 26).

Figure 10B:
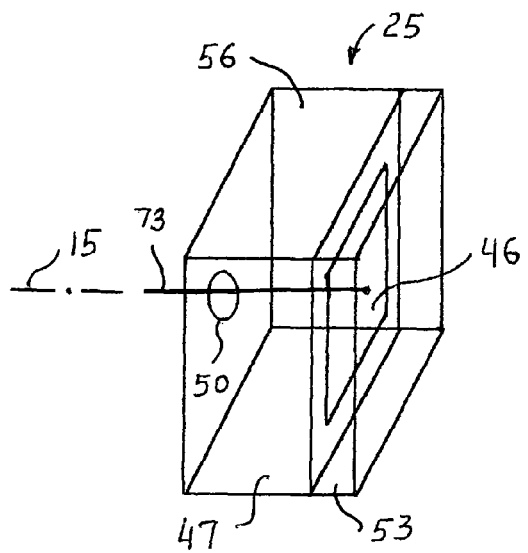
FIG. 10b is a simplified drawing of the first light detection means with the first shielding means.
Figure 10C:
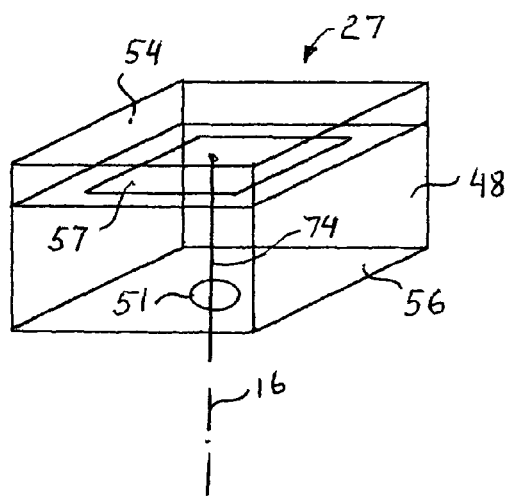
FIG. 10c is a simplified drawing of the second light detection means with the second shielding means.
Figure 10D:
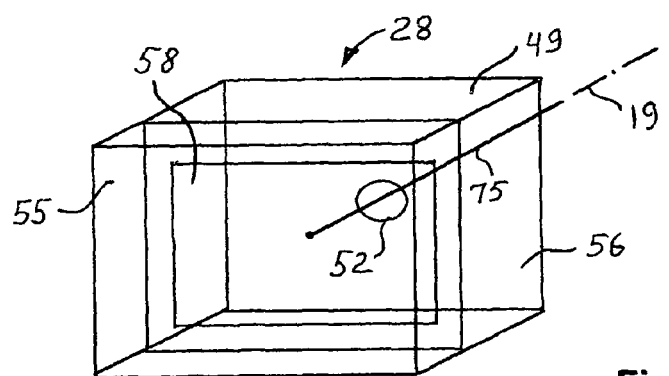
FIG. 10d is a simplified drawing of the third light detection means with the third shielding means.

The FIGS. 10b-10d illustrate the simplified assembly of the first light detection means 25, second light detection means 27 and third light detection means 28 respectively. According to FIG. 10b, the first light detection means 25 includes a first light registering means 53 (e.g., a photodiode, etc.), comprising a first photoelement 46, and a first shielding means 47 including a first aperture 50. The first aperture 50 is located on the first light beam axis 15 and is intended for the unobstructed passage of the first light (laser) beam 73 from the first light beam source 11 along the axis 15 to the first photoelement 46 of the first light registering means 53 of the first light detection means 25. The sides of the first shielding means 47 can overlap the sides of the first light registering means 53 in order to avoid any entering of the possible background light into the first light detection means 25, thereby, minimizing the possible light noise on the first photoelement 46 of the first light registering means 53 of the first light detection means 25. The inside and outside of the first shielding means 47 can be coated (painted, etc.) by the black flat (mate, rough) coating 56, absorbing possible reflected (scattered) light, thereby, eliminating possible light background (light noises).

Referring FIG. 10c, the second light detection means 27 includes a second light registering means (e.g., a photodiode, etc.) 54, comprising a second photoelement 57, and a second shielding means 48 including a second aperture 51. The second aperture 51 is located on the second light beam axis 16 and is intended for the unobstructed passage of the second light (laser) beam 74 from the second light beam source 13 along the axis 16 to the second photoelement 57 of the second light registering means 54 of the second light detection means 27. The sides of the second shielding means 48 can overlap the sides of the second light registering means 54 in order to avoid any entering of the possible background light into the second light detection means 27, thereby, minimizing the possible light noise on the second photoelement 57 of the second light registering means 54 of the second light detection means 27. The inside and outside of the second shielding means 48 can be coated (painted, etc.) by the black flat (mate, rough) coating 56, absorbing possible reflected (scattered) light, thereby eliminating possible light background (light noises).

Referring FIG. 10d, the third light detection means 28 includes a third light registering means (e.g., a photodiode, etc.) 55, comprising a third photoelement 58, and a third shielding means 49 including a third aperture 52. The third aperture 52 is located on the third light beam axis 19 and is intended for the unobstructed passage of the third light (laser) beam 75 from the third light beam source 14 along the axis 19 to the third photoelement 58 of the third light registering means 55 of the third light detection means 28. The sides of the third shielding means 49 can overlap the sides of the third light registering means 55 in order to avoid any entering of the possible background light into the third light detection means 28, thereby, minimizing the possible light noise on the third photoelement 58 of the third light registering means 55 of the third light detection means 28. The inside and outside of the third shielding means 49 can be coated (painted, etc.) by the black flat (mate, rough) coating 56, absorbing possible reflected (scattered) light, thereby eliminating possible light background (light noises).

The wall with the aperture of each shielding means is located on the appropriate light beam axis between the appropriate light registering means and the point of intersection of the axis of the particle flow tubular means 3 with that appropriate light beam axis.

The diameters of the apertures 50, 51, 52 can preferably be slightly bigger than the diameter of the light beams 73, 74, 75 respectively. The shielding means 47-49, as well as the apertures 50-52 minimize the light noises on the appropriate light detection means. For example, the first shielding means 47 and the first aperture 50 minimizse/reduce (on the first photoelement 46 of the first light registering means 53 of the first light detection means 25) the light noise created by the second light beam 74 of the second light beam source 13 and by third light beam 75 of the third light beam source 14. Analogously, the second shielding means 48 and the second aperture 51 reduce (on the second photoelement 57 of the second light registering means 54 of the second light detection means 27) the light noise created by the first light beam 73 of the first light beam source 11 and by third light beam 75 of the third light beam source 14. The third shielding means 49 and the third aperture 52 reduce (on the third photoelement 58 of the third light registering means 55 of the third light detection means 28) the light noise created by the first light beam 73 of the first light beam source 11 and by second light beam 74 of the second light beam source 13.

It is understandable, that not only the shielding means (e.g., 47, 48, 49) and/or the apertures 50, 51, 53 (respectively) can be used, but the other principles and/or means of the light noise reduction and/or elimination can be used too.

Also it is understood that the chamber, shielding means and/or apertures, etc can be of any reasonable configuration (form), size, and material.

The FIG. 11 illustrates the schematic of the improved apparatus. In FIG. 11 are conditionally shown the means intended for multi-measurement (e.g., three coordinate X, Y, Z measurements) of the flowing agents/particles provided by three light detection means, i.e. the first 25, second 27 and third 28 light detection means. According to FIG. 11, the improved apparatus for biomedical agent multi-dimension measuring and analysis includes a chamber 12 comprising a first light detection means 25, a second light detection means 27 and a third light detection means 28, each of which is connected to the light detection signal amplifying means (AM) 36. Also, the chamber 12 (e.g., the outlet end 65 [not shown in FIGS. 11, 12] of the uninterrupted or interrupted particle flow tubular means 26 [not shown in FIGS. 11, 12]) is coupled by the specimen delivery means 66 with the free-surface microfluidic means 29. The free-surface microfluidic means 29 is coupled with the SERS 30, which includes a Raman laser means (LM) 67 and a scattered light Raman detecting means (SDM) 68. The SERS is connected to the light detection signal amplifying means (AM) 36. The light detection signal amplifying means 36 connected to the amplified signal processing means (SPM) 37 which connected to the particle/agent form recognition means (FRM) 38 and to the biomedical analytical means (BMM) 40. The particle form recognition means 38 is connected to the particle/agent form imaging means (FIM) 39. The biomedical analytical means 40 is also connected to the chemical analysis means 31, infrared analysis means 32, radioactive radiation (e.g., radiation level detectors/register, X-Ray, etc.) analysis means 33, magnetic ana-lysis means 34, spectroscopic means 35, and can be connected to other analysis means, for instance, such as: visible (not shown), ultraviolet (not shown), and other electromagnetic radiation absorption means (not shown), liquid chromatography means (not shown), flame ionization analysis means (not shown), DNA melting point means (not shown), or titration analysis means (not shown), etc. The improved apparatus can also comprise a detector that detects the emission spectra from excited SERS probes, etc. The particle/agent form imaging means 39 and the biomedical analytical means 40 are connected to the information processing, control and displaying means (IPM) 44. Also, the light detection devices (not shown) that detects the presence of analyte species by a methods selected from the group consisting of Raman spectroscopy or SERS measurements on a substrate fixed to the microchannel walls (not shown) or in the bulk liquid solution contained within the microchannel (not shown) can provide the electrochemical analysis techniques (not shown), fluorescent chemical marker techniques (not shown), fluorescence quenching (not shown), redox-labeled nucleic acid binding techniques (not shown), mass spectroscopy techniques (not shown), liquid chromatography techniques (not shown), flame ionization analysis techniques (not shown), oscillatory spectral detection techniques (not shown), etc. Some means of the improved apparatus presented by FIG. 11 can communicate to each other wirelessly (not shown) [e.g., the particle form imaging means 39, biomedical analytical means 40, etc. can wirelessly communicate with the information processing, control and displaying means 44).

The FIG. 12 illustrates the schematic of the improved apparatus comprising the appropriate data (e.g., digital data, etc.) interchange ability via the multiplexed bus 45. According to FIG. 12, the amplified signal processing means 37, the particle/agent form recognition means 38, particle/agent form imaging means 39, the biomedical analytical means 40, the microprocessing means (MP) 82 and the terminal means (TM) 76 of the information processing, control and displaying means 44 communicate to each other via multiplexed bus 45. The displaying means (DM) 77, floppy disk means (FD) 78, memory (M) 79, printing means (PM) 80, control panel (CP) 81 (e.g., keyboard, etc.), and compact disk means (CD) 87 of the terminal means 76 communicate by the multiplexed bus 45 too. Some means of the improved apparatus presented by FIG. 12 can communicate to each other wirelessly (not shown) [e.g., at least the means which communicate via multiplexed bus 45 can wirelessly [not shown] communicate to each other).

Figure 13B:
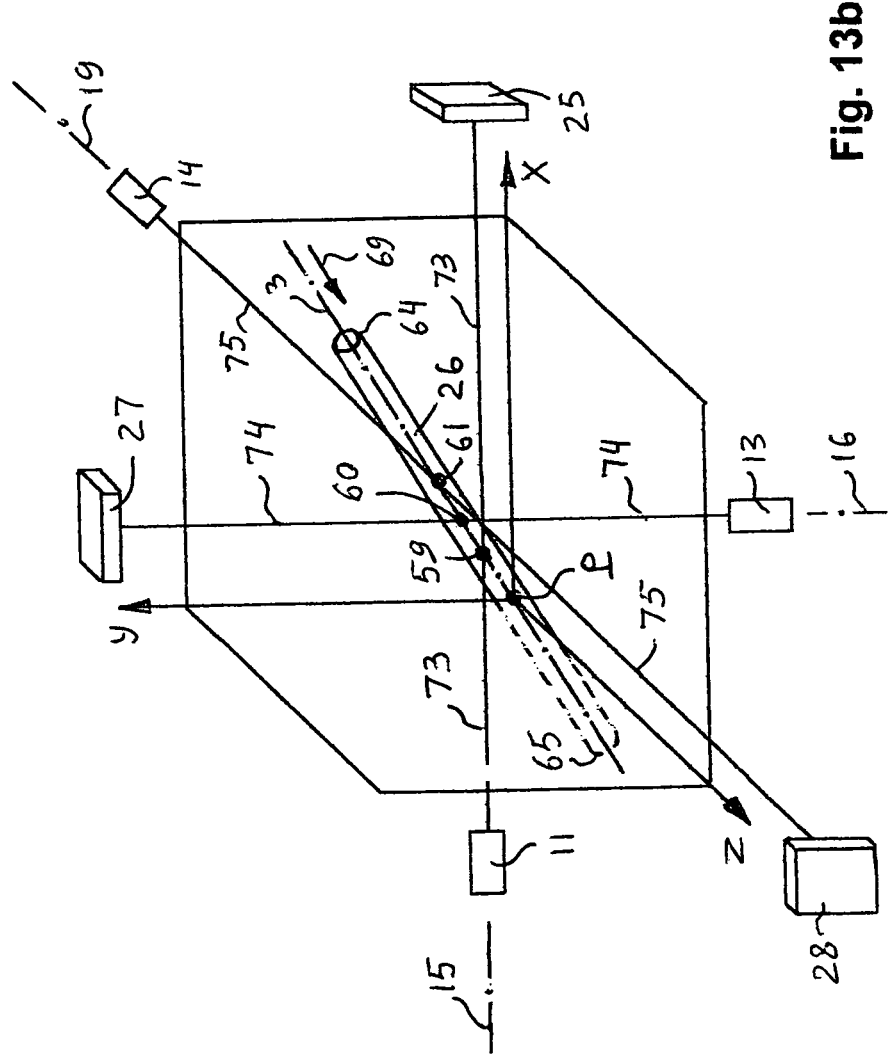
FIG. 13b is a simplified second illustration of the light beam emissions, light detection means and uninterrupted particle flow means disposition and their axes intersection.

As it was mentioned hereinabove, the FIG. 8 conditionally shows the coincidence of the first light beam axis 15 of the first light beam source 11 with the axis X of the coordinate system XYZ, the second light beam axis 16 of the second light beam source 13 with the axis Y of the coordinate system XYZ, and the third light beam axis 19 of the third light beam source 14 with the axis Z of the coordinate system XYZ, but as it is shown in FIG. 13a the common point 20 (see the point 20 also in FIGS. 8, 9a-10a) of the intersection of the particle/agent flow axis 3 with the first light beam axis 15, second light beam axis 16 and third light beam axis 19 can be not located in the point "P" of intersection of the axes X, Y and Z. Also, the particle/agent flow axis 3, first light beam axis 15, second light beam axis 16 and third light beam axis 19 can not intersect each other at the same (common) point. The FIG. 13b shows that the first light beam axis 15, second light beam axis 16 and third light beam axis 19 intersect the particle/agent flow axis 3 at the different points, i.e. it is conditionally shown that the first light beam axis 15 intersects the particle/agent flow axis 3 at the first point 59 on axis 3, the second light beam axis 16 intersects the particle/agent flow axis 3 at the second point 60 on axis 3, and the third light beam axis 19 intersects the particle/agent flow axis 3 at the third point 61 on axis 3. The first 11, second 13 and third 14 light beam sources can simultaneously generate all light (laser) beams (e.g., the first light beam 73, second light beam 74 and third light beam 75 respectively) when they intersect each other and the particle flow axis 3 at one common point (for example, at the point 20, as it is conditionally shown in FIGS. 8, 10a, 13a) or can generate the light beams (e.g., 73, 74, 75) in the predetermined synchronized sequence when each light beam 73, 74, 75 intersects the particle flow axis 3 at the different points (for example, at the points 59, 60, 61 respectively, as it is conditionally shown in FIG. 13b [see also FIGS. 14, 15]).

The predetermined synchronized sequence of the light sources' operation is correlated with the particle flow velocity.

It is understood, that the synchronized operation of the light beam sources in sequence can reduce the light background (light noise).

The improved methods provide the following operation of the improved apparatus for biomedical agent multi-dimension measuring and analysis.

The pumping means (not shown) or blowing means (not shown), etc. provides the assaying of the substance (specimen, particles, etc.) and a flow of the assayed specimen, for example in the direction 69 (FIGS. 8, 13a,b, 14, 15, 16), through the particle flow tubular means 26 along the particle flow axis 3. It is understood, that the particle flow can be provided in the reversed direction (not shown).

In the illustrations and drawings of this invention, as an example, are conditionally presented the three-dimension (X, Y, Z) measuring of the particles within the assayed specimen and those particle form possible imaging, but there can be other multi-dimension principles of the particle/agent measuring and particle imaging remaining the teaching of the present invention.

Figure 15:
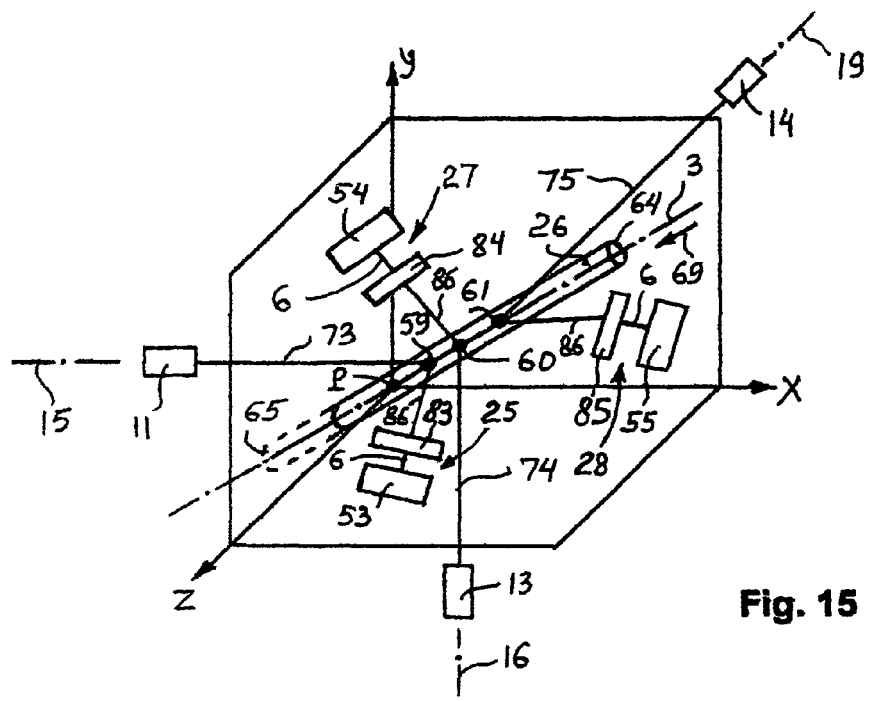
FIG. 15 is a simplified illustration of the improved apparatus for the scattered light collection principles.

The light (laser) beam sources 11, 13 14 (e.g., the laser diodes, etc.) produce the light (laser) beams 73, 74, 75 respectively along the axes 15, 16, 19 respectively. Each of the axes 15, 16 and 19 intersects a particle flow axis 3. The intersection of the light beam axes 15, 16, 19 with the particle flow axis 3 can occur within the particle monitoring region inside the chamber 12 at a single point 20 on the particle flow axis 3 (FIGS. 8, 10a, 13a) or at the different points, e.g., at the points 59, 60, 61 (FIGS. 13b, 14, 15).

Each light beam is directed to the appropriate light detection means, for instance, the first light beam along the first light beam axis 15 is directed to the first light detection means 25, the second light beam along the second light beam axis 16 is directed to the second light detection means 27, and the third light beam along the third light beam axis 19 is directed to the third light detection means 28. The first light detection means 25 is located on the first light beam axis 15, and the point 20 (FIGS. 8, 10a, 13a) or point 59 (FIGS. 13b, 14, 15) of the intersection of the first light beam axis 15 with the particle flow axis 3 is located between the first light beam source 11 and the first light detection means 25. Thus, when the particle, flowing along particle flow axis 3, intersects the first light beam, such particle obstructs the light directed to the first light detection means 25, thereby reducing the intensity of the light on the first photoelement 46 of the first light registering means 53 of the first light detection means 25.

The second light detection means 27 is located on the second light beam axis 16, and the point 20 (FIGS. 8, 10a, 13a) or point 60 (FIGS. 13b-15) of the intersection of the second light beam axis 16 with the particle flow axis 3 is located between the second light beam source 13 and the second light detection means 27. Thus, when the particle, flowing along particle flow axis 3, intersects the second light beam, such particle obstructs the light directed to the second light detection means 27, thereby reducing the intensity of the light on the second photoelement 57 of the second light registering means 54 of the second light detection means 27.

The third light detection means 28 is located on the third light beam axis 19, and the point 20 (FIGS. 8, 10a, 13a) or point 61 (FIGS. 13b-15) of the intersection of the third light beam axis 19 with the particle flow axis 3 is located between the third light beam source 14 and the third light detection means 28. Thus, when the particle, flowing along particle flow axis 3, intersects the third light beam, such particle obstructs the light directed to the third light detection means 28, thereby reducing the intensity of the light on the third photoelement 58 of the third light registering means 55 of the third light detection means 28.

It means, that when the particles of the particle flow intersect the light beam, the intensity of the light beam on the light detection means will be less than at the time when the particles are missing, because the presence of a particle in the light beam is an obstruction for the light in the direction to the light detection means. Thus, the light detection means detects the intensity of the light behind the particle (the "shadow" of the particle). The bigger particle, the less light intensity on the light detection means (the less amplitude of the light detection means), and the bigger particle, the longer it obstructs the light from the light source and, as it is well understanddable, the longer duration of that reduced light intensity on the light detection means, and, as a result, the longer duration of the outputs 70, 71, 72 (FIGS. 11, 12) of the light detection means 25, 27, 28 respectively.

Also, it is understood, that other light detection principles (methods) can be used in the improved apparatus. For example, for scattered light collection by lens 10 (FIG. 16) (or by mirror or direct collection system [not shown in FIG. 16]), the light intensity of the scattered light on the light detection means (on the light detector [e.g., photodetector, etc.]) will be presented when the particles intersect the laser (light) beam. The bigger particle, the higher light intensity on the light detection means. The higher light intensity on the light detection means, the higher amplitude and longer duration of the outputs 70, 71, 72 (FIGS. 11, 12) of the light detection means 25, 27, 28 respectively.

According to FIG. 11, for instance, the outlet end 65 of the particle flow tubular means 26 of the chamber 12 is coupled by the specimen delivery means 66 with the free-surface fluidic (microfluidic) means 29. The coupling of the outlet end 65 of the particle flow tubular means 26 with the free-surface fluidic (microfluidic) means 29 can be provided by any reasonably convenient principles of coupling. The specimen delivery means 66 can be of any reasonable configuration, for instance, the specimen delivery means 66 can be presented by the flexible tubular means [not shown], etc. Also, as it has been mentioned hereinabove, the free-surface fluidic means 29 can extend (not shown) from the particle flow tubular means 26 (e.g., from the outlet end 65 of the particle flow tubular means 26). The free-surface fluidic means 29 is coupled with the SERS 30. Additionally, the tempera-ture measuring means (not shown) and/or particle flow velocity measuring means (not shown) [e.g., flow meter, etc.], etc. can be coupled with the chamber 12 or with the particle flow tubular means 26 or with the specimen delivery means 66 or in any reasonable and convenient place of the improved apparatus. Thus, the temperature measuring means (not shown) and/or particle flow velocity measuring means (not shown) can be integrated into the improved apparatus or juxtaposed at a particular region of the improved apparatus.

The outputs (output signals) 70, 71, 72 from the light detection means 25, 27, 28 respectively and output (signal(s)) from SERS 30 follow to the light detection signal amplifying means 36. The amplified signals from the light detection signal amplifying means 36 follow to the amplified signal processing means 37. From the amplified signal processing means 37 the initially processed signals follow to the particle form recognition means 38, where the multi-dimension characteristics (e.g., three-dimension measurement) of each particle are combined into measurement information (data), and the particles' multi-dimension measurement characteristics are selected and sorted in the groups by the particle identical measurement information (i.e. by the identical three-dimension size). Also, the particle form recognition means 38 provides the counting of the particles in each size group and/or provide the analysis of concentration of the particle in a priory predetermined volume of the assayed specimen. The initially processed signals from the amplified signal processing means 37 also follow to the biomedical analytical means 40, in which also follow the signals from the chemical analysis means 31, infrared analysis means 32, radioactive radiation analysis means 33, magnetic analysis means 34, spectroscopic means 35. These means do not limit the equipment which can operate together with the mentioned hereinabove means and the signals from the other used means, devices and apparatus, which are not presented (not shown) in the FIGS. 11, 12 (e.g., ultraviolet [not shown], and other electromagnetic radiation absorption means (not shown), liquid chromatography means [not shown], flame ionization analysis means [not shown], DNA melting point means [not shown], or titration analysis means [not shown], etc.) can follow to the appropriate means presented in the schematics in FIGS. 11, 12.

Further, the signal from the particle form recognition means 38 through the particle form imaging means 39 follow to the information processing, control and displaying means 44, in which also follow the signals from the biomedical analytical means 40.

Referring to the FIG. 12, the data (information) exchange between the amplified signal processing means 37, the particle form recognition means 38, particle form imaging means 39, the biomedical analytical means 40, the microprocessing means 82 and the terminal means 76 of the information processing, control and displaying means 44, and also displaying means 77, floppy disk means 78, memory 79, printing means 80, control panel 81, and compact disk means 87 of the terminal means 76 is provided by the multiplexed bus 45. It is understood, that the address bus (not shown) and data bus (not shown) can be used instead of the multiplexed bus 45.

It should be understandable, that the functions of the means presented in FIGS. 11 and 12 are not limited to the described in this invention and can be equivalently inter-distributed (inter-redistributed) between each other, still teaching of the improved apparatus of the present invention.

Referring to FIG. 15, the improved apparatus uses the optic collection means: the first light collection optic means 83, the second light collection optic means 84 and the third light collection optic means 85 for the scattered light collection. Each scattered light collection optic means (i.e. each of 83, 84, 85) is conditionally, as an example, can be represented by the lens(es) 10 [FIG. 16], but the other light collection principles and means can be used. Each optic collection means is located between the appropriate light registering means and the appropriate point of intersection of the appropriate light beam with the particle flow axis 3.

According to FIG. 15, the assembly of each of the light emitting-detecting portions includes: a first light emitting-detecting portion comprises a first light beam source 11—light detection means 25, including the first scattered light collection optic means 83 and first registering means 53, including a first photoelement 46; a second light emitting-detecting portion comprises a second light beam source 13—light detection means 27, including the second scattered light collection optic means 84 and second registering means 54, including a first photoelement 57; and a third light emitting-detecting portion comprises first light beam source 14—light detection means 28, including the third scattered light collection optic means 85 and third registering means 55, including a first photoelement 58. All three emitting-detecting portions are generally and conditionally represented in FIG. 16 only by the simplified assembly for the first light emitting-detecting portion (first light source 11—first light detection means 25), because the assemblies for second and third emitting-detecting portions are analogous to the assembly of the first emitting-detecting portion.

Figure 16:
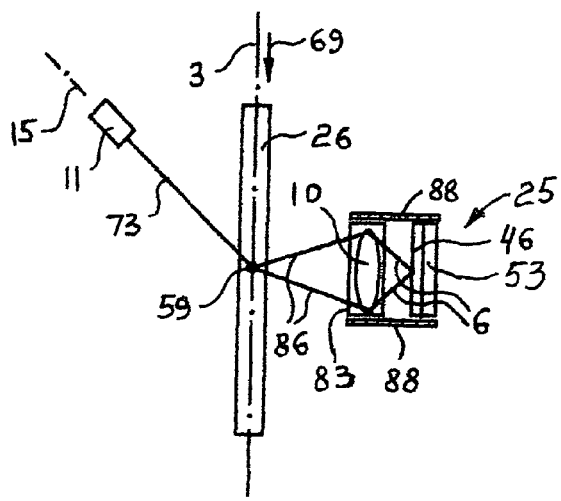
FIG. 16 is a simplified illustration of the light detection means for the scattered light collection.

In the FIG. 16, is conditionally shown that the lens 10 and light registering means 53 are covered (e.g., in the manner analogous as the shielding means 47-49 have been used), by some kind of cover 88 (e.g., similar to the shielding means 47-49). It is understandable, that not only the cover 88 can be used for the light noise reduction, but the other principles and/or means of the light noise reduction and/or elimination can be used too. Also, it is understood that the cover can be of any reasonable configuration (form), size, and material.

It is also understood, that the walls with the apertures (e.g., apertures 50, 51, 52) of the light detection means can not be significantly useful when the scattered light collection principles are used, and therefore, are not included and not shown in FIG. 16. The scattered light 86 is collected by the light collection optic means 83 (FIG. 16) which is conditionally, as an example, presented by the single biconvex lens 10, but the other types of lenses (not shown) or system of lenses [not shown in FIG. 16], as well as the mirror(s) (not shown) or light detector(s) (not shown), directly detecting the scattered light, can be successfully used too. The collected scattered light 6 is focused on the photoelement 46 of the light registering means 53 of the light detection means 25.

As it has been mentioned hereinabove, the inlet end (not shown) of the free-surface microfluidic means 29 (FSFM) for the biomedical particle (analyte) analysis can be extended (not shown) from the outlet end 65 of the particle flow tubular means 26 (see FIGS. 8, 13a,b) or can be coupled (FIGS. 11, 12) with the particle flow tubular means 26 (e.g., with the outlet end 65 [not shown in FIGS. 11, 12] of the particle flow tubular means 26), but it is understandable from the present invention that there is an another variant (another embodiment) of the improved methods and apparatus when the same multi-dimension particle measuring means (e.g., shown in FIGS. 8-16), e.g., including the light beam sources 11, 13, 14, light detection means 25, 27, 28 and the other appropriate and relevant means [e.g., such as the shielding means 47, 48, 49 with the apertures 50, 51, 52 [not shown in FIG. 17] and the optic means 83, 84, 85 [not shown in FIG. 17], etc.) are operate directly with the free-surface microfluidic means (FSFM) 29 (FIG. 17) instead of the particle flow tubular means 26, utilizing not enclosed free-surface fluidics (without chamber 12). In compliance with this embodiment, the mentioned multi-dimension particle measuring means e.g., the light beam sources 11, 13, 14, light detection means 25, 27, 28 and the other appropriate and relevant means (e.g., such as the optic means 83, 84, 85 [not shown in FIG. 17]), etc. can locate at the distal (not shown) or proximal areas with respect to the location of the Raman laser means 67 and scattered light Raman detecting means 68, as it is shown in FIG. 17.

Figure 17:
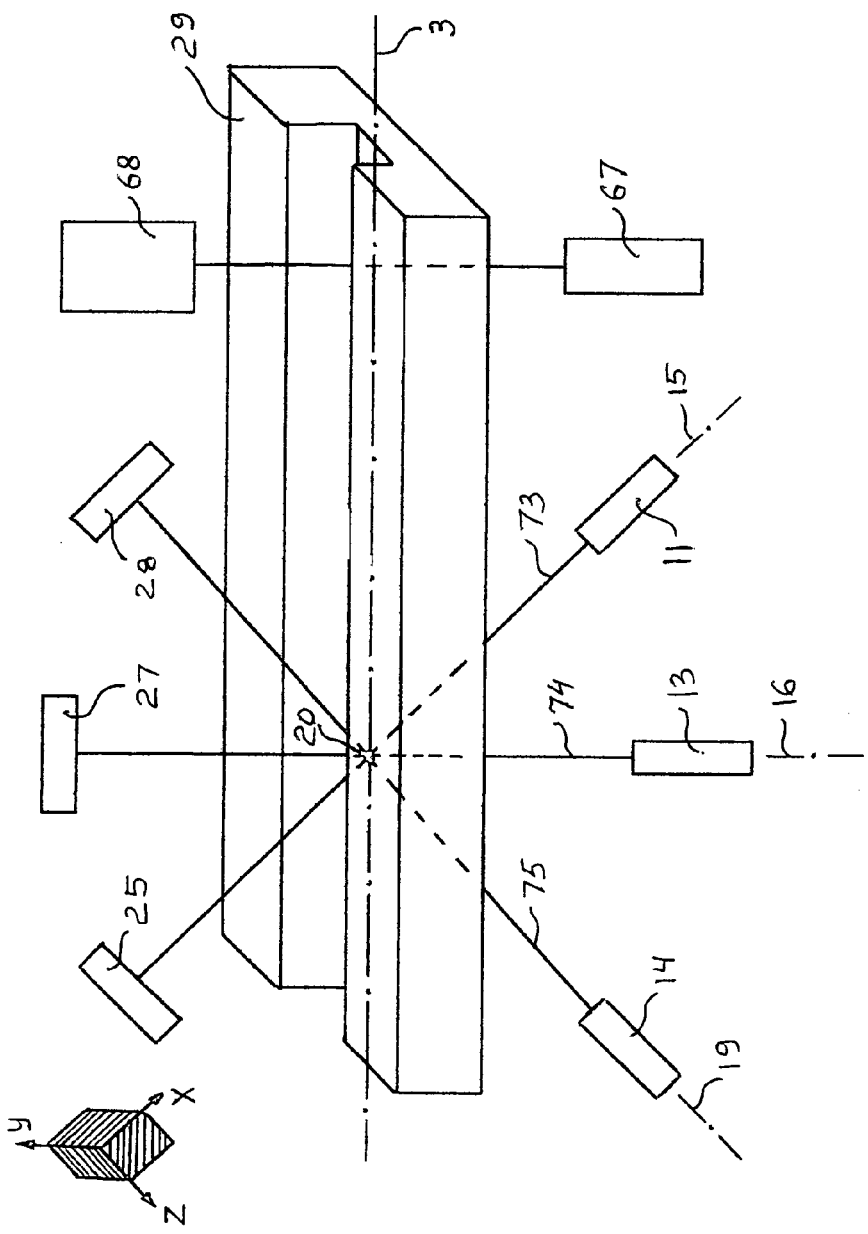
FIG. 17 is a simplified illustration of the multi-dimension measuring of the biomedical agents flowing through the free-surface microfluidic means.

Also, referring to FIG. 17, the light beams 73, 74, 75 (along the axes 15, 16, 19 respectively) intersect the particle (microfluidc) flow axis 3 of the FSFM 29, which is placed horizontally. According to the system coordinate XYZ, shown in the left top corner of FIG. 17, the light radiation for the first light beam 73 is in the direction of axis −X, the light radiation for the second light beam 74 is in the direction of axis Y, and the light radiation for the third light beam 75 is in the direction of axis −Z. Thus, the light emitting-detecting system for the light beam sources 11, 13, 14, conditionally shown in FIG. 17, operates in the coordinate system "−XY-Z".

The schematics of the improved apparatus with the FSFM (not shown) include the same architecture and means, as shown in FIGS. 11, 12, except the chamber 12.

Also, it is understandable, that not only one time multi-dimension (e.g., 3-D) measurement can be produced during each particle monitoring, but there can be produced a plurality of the 3-D measurements of each single particle (multi-dimensional scanning [e.g., 3-D scanning] of each particle). The more intensive scanning of each particle is produced (the higher frequency of the scanning), the higher precision of the particle form/shape and the image of each particle.

It should be understandable, that in the FIGS. 7-15, as an example, has been used the coordinate system XYZ, but it can, for example, be used the coordinate system −XY-Z with the coordinate axes −X, Y, −Z (FIG. 17) or any other coordinate systems with any axes X, −X, Y, −Y, Z, −Z combination.

The images (presentation) of all means (components) in FIGS. 1-16 are presented conditionally and may mostly not depict the real image/shape of the real means, for example, the light source means are conditionally presented in the elongated configuration for convenience of illustration.

Also it is understood that mentioned in this disclosure means, components, etc. can be of any reasonable configuration (form), size, and material.

The improved multi-dimension measurement methods and apparatus realizing the multi-measurement(s) are significantly needed to distinguish and recognize the different categories (groups) of the agents (e.g., categories of the cells, microbes or any biomedical agent(s) and their formations, environmental contamination, etc.) by their form (shape) and particularly by the same style (type) of the regular or irregular configuration (form) during their analysis, and needed to define the quantity of the identical 3-D dimension and/or identical form particles, their concentration and/or periodicity (distance), etc.

CONCLUSION, RAMIFICATION AND SCOPE

Accordingly the reader will see that, according to the invention, an improved methods and apparatus for biomedical agent multi-dimension measuring and analysis are provided. There has thus been outlined, rather broadly, the more important features of the invention. In this respect, it is understood that the invention is not limited in its application to the details of steps, construction/structures and to the arrangements of the components/means set forth in the description and/or drawings. The invention is capable of other embodiments and of being practiced and carried out in various ways. Also, it is to be understood that the phraseology and terminology employed herein are for the purpose of description and should not be regarded as limiting.

While the above description contains many specificities, these should not construed as limitations on the scope of the invention, but as exemplification of the presently-preferred embodiments thereof. Many other ramifications are possible within the teaching to the invention. For instance, the improved methods can be fully and successfully used for the particle measuring and counting apparatus/systems (also known as the particle counters) operation, for example, in the cleanrooms, for contamination control industry in the fields of semiconductor, pharmaceutical and other industries, as well as the particle counters in the hazardous chemicals or explosive areas.

The persons of ordinary skills and/or creativity in the art will readily observe that numerous modifications and advantages of the improved methods and apparatus for biomedical agent multi-dimension measuring and analysis may be made while retaining the teachings of the invention.

As such, those skilled in the art will appreciate that the conception, upon which this disclosure is based, can readily be utilized as a basis for the designing of other structures, for carrying out the several purpose of the present invention. It is important, therefore, that the claims be regarded as including such equivalent constructions insofar as they do not depart from the spirit and scope of the present invention.

THE DRAWING REFERENCE NUMERALS

1.—a device axis;
2.—a single light beam axis;
3.—a particle flow axis [an axis of flow of particles];
4.—a single light detection means;
5.—a plurality (or large size) of light detection means;
6.—a collected scattered light;
7.—unfocused scattered light;
8.—a first focal point;
9.—a second focal point;
10.—a lens;
11.—a first light beam source [a first source of a light beam];
12.—a chamber;
13.—a second light beam source [a second source of a light beam];
14.—a third light beam source [a third source of a light beam];
15.—a first light beam axis [an axis of a first beam of light];
16.—a second light beam axis [an axis of a second beam of light];
17.—a non-divergent (ellipsoidal) mirror;
18.—a divergent quadric (paraboloidal) mirror;
19.—a third light beam axis [an axis of a third beam of light];
20.—a common point of intersection of the axes 15, 16, 19 intersection;
21.—a XPZ plane;
22.—a XPY plane;
23.—unconsidered scattered light;
24.—a YPZ plane;
25.—a first light detection means (LDM 1) [a first means of detection of light];
26.—a particle flow tubular means;
27.—a second light detection means (LDM 2) [a second means of detection of light];
28.—a third light detection means (LDM 3) [a third means of detection of light];
29.—a free-surface fluidic means (FSFM);
30.—a Surface Enhanced Raman Scattering (SERS);
31.—a chemical analysis means (CM);
32.—an infrared analysis means (IM);
33.—a radioactive radiation analysis means (RM).
34.—a magnetic radiation analysis means (MM);
35.—a spectroscopic means (SP);
36.—a light detection signal amplifying means (AM);
37.—an amplified signal processing means (SPM);
38.—a particle form recognition means (FRM);
39.—a particle form imaging means (FIM);
40.—a biomedical analytical means (BMM);
41-41.—a view (FIGS. 8, 9a);
42-42.—a view (FIGS. 8, 9b);

43-43.—a view (FIGS. 8, 9*c*);
44.—an information processing, control and displaying means (IPM);
45.—a multiplexed bus;
46.—a first photoelement;
47.—a first shielding means;
48.—a second shielding means;
49.—a third shielding means;
50.—a first aperture;
51.—a second aperture;
52.—a third aperture;
53.—a first light registering means [a first registering means of a light];
54.—a second light registering means [a second registering means of a light];
55.—a third light registering means [a third registering means of a light];
56.—a black flat mate coating;
57.—a second photoelement;
58.—a third photoelement;
59.—a first point on the axis 3 (intersection of the axes 3 and 15);
60.—a second point on the axis 3 (intersection of the axes 3 and 16);
61.—a third point on the axis 3 (intersection of the axes 3 and 19);
62.—an inlet portion of interrupted 26;
63.—an outlet portion of interrupted 26;
64.—an inlet end of 26;
65.—an outlet end of 26;
66.—a specimen delivery means;
67.—a Raman laser means (LM);
68.—a scattered light Raman detecting means (SDM);
69.—a direction of the assayed specimen (particles) flow;
70.—an output of the first light detection means;
71.—an output of the second light detection means;
72.—an output of the third light detection means;
73.—a first light beam;
74.—a second light beam;
75.—a third light beam;
76.—a terminal means (TM);
77.—a display means (DM);
78.—a floppy disk means (FD);
79.—a memory (M);
80.—a printing means (PM);
81.—a control panel (CP);
82.—a microprocessing means (MP).
83.—a first light collection optic means [a first optic means of collection of a light];
84.—a second light collection optic means [a second optic means of collection of a light];
85.—a third light collection optic means [a third optic means of collection of a light];
86.—a scattered light;
87.—a compact disk means (CD);
88.—a cover;
P—a point of intersection of the axes X, Y, Z;
P1—a point of intersection of the axes X and Z;
P2—a point of intersection of the axes X and Y;
P3—a point of intersection of the axes X and Y.

What is claimed is:

1. A method for biomedical agent multi-dimension measuring and analysis comprising the steps of providing at least two light beam sources of a plurality of light beam sources, wherein a first light beam source provides a first light beam along a first light beam axis and a second light beam source provides a second light beam along a second light beam axis;

providing a flow of said biomedical agent along a biomedical agent flow axis through a biomedical agent monitoring region;

providing a first intersection of said biomedical agent flow axis with said first light beam axis at a first point on said biomedical agent flow axis within said biomedical agent monitoring region;

providing a second intersection of said biomedical agent flow axis with said second light beam axis at a second point on said biomedical agent flow axis within said biomedical agent monitoring region, wherein a location of said second point on said biomedical agent flow axis is different from location of said first point on said biomedical agent flow axis;

providing a detection of a light, which is created during said first intersection, by said first light detection means, wherein said light is a scattered light created by said biomedical agent flowing through said first point located within said biomedical agent monitoring region;

providing a detection of a light, which is created during said second intersection, by said second light detection means, wherein said light is said scattered light created by said biomedical agent flowing through said second point located within said biomedical agent monitoring region;

providing by said first light detection means an output which is effectively indicative of a first dimension of said biomedical agent flowing through said first point;

providing by said second light detection means an output which is effectively indicative of a second dimension of said biomedical agent flowing through said second point;

processing the outputs from said first light detection means and from said second light detection means providing said multi-dimension measuring of said biomedical agent and said analysis of said biomedical agent, wherein said analysis includes at least a counting of the biomedical agents, defining a concentration of the biomedical agents, a radioactive absorption testing, a X-Ray absorption testing, an infrared testing, an ultraviolet testing, a magnetic testing, an electromagnetic testing, an electromagnetic radiation absorption testing, a mass spectroscopy testing, a liquid chromatography testing, a flame ionization testing, a chemical testing, a DNA melting point testing, a DNA titration testing, an electrochemical testing, a fluorescent chemical testing, a fluorescence quenching testing, a redox-labeled nucleic acid binding testing, an oscillatory spectral detection testing.

2. The method of claim 1, wherein further said first light beam source provides a first scanning light beam which provides a scanning of each biomedical agent flowing through said first point within said biomedical agent monitoring region and said second light beam source provides a second scanning light beam which provides said scanning of said each biomedical agent flowing through said second point within said biomedical agent monitoring region, and wherein said scanning by said first scanning light beam of each biomedical agent flowing through said first point within said biomedical agent monitoring region and said scanning by said second scanning light beam of said each biomedical agent flowing through said second point within said biomedical agent monitoring region are provided in a synchronized sequence.

3. The method of claim 1, wherein further said method provides at least three light beam sources of a plurality of light beam sources, wherein said first light beam source provides said first light beam along said first light beam axis, said second light beam source provides said second light beam along said second light beam axis and a third light beam source provides a third light beam along a third light beam axis;
  providing a third intersection of said biomedical agent flow axis with said third light beam axis at a third point on said biomedical agent flow axis within said biomedical agent monitoring region, wherein a location of said third point on said biomedical agent flow axis is different from location of said first point on said biomedical agent flow axis and from location of said second point on said biomedical agent flow axis;
  providing a detection of a light, which is created during said third intersection, by a third light detection means, wherein said light is a scattered light created by said biomedical agent flowing through said third point located within said biomedical agent monitoring region;
  providing by said third light detection means an output which is effectively indicative of a third dimension of said biomedical agent flowing through said third point;
  processing the outputs from said first light detection means, from said second light detection means and from third light detection means providing said multi-dimension measuring of said biomedical agent and said analysis of said biomedical agent, wherein said analysis includes at least a counting of the biomedical agents, defining of a concentration of the biomedical agents, a radioactive absorption testing, a X-Ray absorption testing, an infrared testing, an ultraviolet testing, a magnetic testing, an electromagnetic testing, an electromagnetic radiation absorption testing, a mass spectroscopy testing, a liquid chromatography testing, a flame ionization testing, a chemical testing, a DNA melting point testing, a DNA titration testing, an electrochemical testing, a fluorescent chemical testing, a fluorescence quenching testing, a redox-labeled nucleic acid binding testing, an oscillatory spectral detection testing.

4. The method of claim 3, wherein further said first light beam source provides a first scanning light beam which provides a scanning of each biomedical agent flowing through a first point within said biomedical agent monitoring region, said second light beam source provides a second scanning light beam which provides said scanning of said each biomedical agent flowing through a second point within said biomedical agent monitoring region and said third light beam source provides a third scanning light beam which provides said scanning of said each biomedical agent flowing through said third point located within said biomedical agent monitoring region, and wherein said scanning by said first scanning light beam of each biomedical agent flowing through said first point within said biomedical agent monitoring region, said scanning by said second scanning light beam of said each biomedical agent flowing through said second point within said biomedical agent monitoring region and said scanning by said third scanning light beam of each biomedical agent flowing through said third point within said biomedical agent monitoring region are provided in a synchronized sequence.

5. An apparatus for biomedical agent multi-dimension measuring and analysis comprising
  a first light emitting-detecting portion including
    a first light beam source, providing a first scanning light beam, wherein said first scanning light beam provides a first intersection of a biomedical agent flow axis with said first scanning light beam at a first point on said biomedical agent flow axis within a biomedical agent monitoring region;
    a first light detection means connected to a light detection signal amplifying means, wherein said first light detection means provides an output which is effectively indicative of a first dimension of said multi-dimension measuring;
  a second light emitting-detecting portion including
    a second light beam source, providing a second scanning light beam, wherein said second scanning light beam provides a second intersection of said biomedical agent flow axis with said second scanning light beam at a second point on said biomedical agent flow axis within said biomedical agent monitoring region, and wherein a location of said second point on said biomedical agent flow axis is different from location of said first point on said biomedical agent flow axis;
    a second light detection means connected to said light detection signal amplifying means, wherein said second light detection means provides an output which is effectively indicative of a second dimension of said multi-dimension measuring;
  a third light emitting-detecting portion including
    a third light beam source, providing a third scanning light beam, wherein said third scanning light beam provides a third intersection of said biomedical agent flow axis with said third scanning light beam at a third point on said biomedical agent flow axis within said biomedical agent monitoring region, and wherein location of said third point on said biomedical agent flow axis is different from location of said first point on said biomedical agent flow axis and from location of said second point on said biomedical agent flow axis;
    a third light detection means connected to said light detection signal amplifying means, providing an amplification of the detected signals from said first light detection means, from said second light detection means and from said third light detection means, wherein said third light detection means provides an output which is effectively indicative of a third dimension of said multi-dimension measuring;
  a free-surface fluidic means coupled with a biomedical agent flow tubular means by a specimen delivery means and coupled at least with a surface enhanced raman scattering means which is connected to said light detection signal amplifying means which amplifies the detection signals from said surface enhanced raman scattering means, with a radioactive radiation analysis means, with an infrared analysis means, with a chemical analysis means, with an electrochemical analysis means, with a magnetic radiation analysis means, with an electromagnetic radiation analysis means, with a radioactive absorption analysis means, with a X-Ray absorption analysis means, with an ultraviolet analysis means, with an electromagnetic radiation absorption analysis means, with a spectroscopic analyzing means, with a mass spectroscopy analysis means, with a liquid chromatography analysis means, with a flame ionization analysis means, with a DNA melting point analyzing means, with a DNA titration analysis means, with a fluorescence quenching analysis means, with a redox-labeled nucleic acid binding analysis means, with an oscillatory spectral detection analysis means, providing said analysis;

an amplified signal processing means, providing an initial processing of the amplified signals, connected to a biomedical agent form recognition means, to a biomedical analytical means, summarizing the analyzed information from the connected analysis means, and to said light detection signal amplifying means, wherein said biomedical analytical means is connected at least to said radioactive radiation analysis means, to said infrared analysis means, to said chemical analysis means, to said electrochemical analysis means, to said magnetic radiation analysis means, to said electromagnetic radiation analysis means, to said radioactive absorption analysis means, to said X-Ray absorption analysis means, to said ultraviolet analysis means, to said electromagnetic radiation absorption analysis means, to said spectroscopic analysis means, to said mass spectroscopy analysis means, to said liquid chromatography analysis means, to said flame ionization analysis means, to said DNA melting point analysis means, to said DNA titration analysis means, to said fluorescence quenching analysis means, to said redox-labeled nucleic acid binding analysis means, and to said oscillatory spectral detection analysis means;

a biomedical agent form imaging means connected to said biomedical agent recognition means which combines said first dimension, said second dimension and said third dimension into an information about said multi-dimension measuring, and selects and sorts an identical measurement information about biomedical agents in the groups with the identical three-dimension measurement, wherein said biomedical agent recognition means provides a counting of the biomedical agents in each size group or provides said analysis of a concentration of the biomedical agents, and wherein said biomedical agent form imaging means provides an initial processing of the scanned information and the information from said biomedical agent recognition means;

an information processing, control and displaying means, providing a final processing of the combined information, connected to said biomedical analytical means and to said biomedical agent form imaging means, wherein said information processing, control and displaying means comprises at least a microprocessing means and a terminal means including a display means, a floppy disk means, a memory, a printing means, a control panel, and compact disk means which are connected to each other by a multiplexed bus or by a data bus and an address bus, wherein said microprocessing means of said information processing, control and displaying means, said biomedical analytical means, said biomedical agent form imaging means, said biomedical agent form recognition means, and said amplified signal processing means are connected to each other and to said terminal means by said multiplexed bus or by said data bus and said address bus.

6. The apparatus of claim 5, wherein further said biomedical agent recognition means provides said counting of the biomedical agents in each size group and provides said analysis of said concentration of the biomedical agents displaying means.

* * * * *